United States Patent
Wasylucha

(10) Patent No.: US 10,285,790 B2
(45) Date of Patent: May 14, 2019

(54) PROCESS OF TOOTH WHITENING AND APPARATUS THEREFOR

(71) Applicant: Bryan Wasylucha, Irvine, CA (US)

(72) Inventor: Bryan Wasylucha, Irvine, CA (US)

( * ) Notice: Subject to any disclaimer, the term of this patent is extended or adjusted under 35 U.S.C. 154(b) by 654 days.

(21) Appl. No.: 14/101,910

(22) Filed: Dec. 10, 2013

(65) Prior Publication Data
US 2014/0099603 A1   Apr. 10, 2014

Related U.S. Application Data

(62) Division of application No. 10/872,256, filed on Jun. 18, 2004, now Pat. No. 8,602,774.

(60) Provisional application No. 60/479,801, filed on Jun. 19, 2003.

(51) Int. Cl.
| | |
|---|---|
| A61C 19/06 | (2006.01) |
| A61C 3/00 | (2006.01) |
| A61K 8/22 | (2006.01) |
| A61Q 11/00 | (2006.01) |
| A61C 13/15 | (2006.01) |
| A61C 19/02 | (2006.01) |
| A61N 5/06 | (2006.01) |
| A46B 11/00 | (2006.01) |
| A61C 5/62 | (2017.01) |
| A61C 5/64 | (2017.01) |

(52) U.S. Cl.
CPC ............ *A61C 19/066* (2013.01); *A61C 3/005* (2013.01); *A61C 19/003* (2013.01); *A61C 19/02* (2013.01); *A61C 19/063* (2013.01); *A61K 8/22* (2013.01); *A61N 5/062* (2013.01); *A61N 5/0603* (2013.01); *A61Q 11/00* (2013.01); *A46B 11/0027* (2013.01); *A46B 2200/1066* (2013.01); *A61C 5/62* (2017.02); *A61C 5/64* (2017.02)

(58) Field of Classification Search
CPC ..... A61C 19/06; A61C 19/063; A61C 19/066; A61C 3/005; A61C 19/003; A61C 19/02; A61C 5/62; A61C 5/64; A61K 8/22; A61N 5/0603; A61N 5/062; A46B 11/0027; A46B 2200/1066; A61Q 11/00
USPC ................. 433/29, 25, 215, 216, 80, 81, 89; 401/143, 141, 172
See application file for complete search history.

(56) References Cited

U.S. PATENT DOCUMENTS

| | | |
|---|---|---|
| 2,635,025 A | 4/1953 | Ziska |
| 2,699,889 A | 1/1955 | Johnson |
| 3,527,646 A | 9/1970 | Scheick |
| 3,796,668 A | 3/1974 | Hickcox |
| 4,043,042 A | 8/1977 | Perfect |

(Continued)

*Primary Examiner* — Heidi M Eide
(74) *Attorney, Agent, or Firm* — David Guerra

(57) ABSTRACT

A process of whitening a tooth provided by the invention includes the steps of providing a delivery device for mechanical dispensing of a predetermined amount of a whitening composition to an applicator tip; dispensing the amount of whitening composition to the applicator tip; applying the amount of whitening composition disposed on the applicator tip to the tooth to be whitened; and allowing the whitening composition to remain in contact with the tooth for a period of time sufficient to whiten the tooth. Optionally, the process further includes the step of exposing the whitening composition to light. A gum or candy for tooth bleaching is detailed along with methods of use. A device adapted to dispense an amount of a dental whitening composition optionally includes a light source for activating the whitener.

17 Claims, 9 Drawing Sheets

(56) References Cited

U.S. PATENT DOCUMENTS

| | | | |
|---|---|---|---|
| 4,156,740 | A | 5/1979 | Glass et al. |
| 4,157,402 | A | 6/1979 | Ogawa et al. |
| 4,184,196 | A * | 1/1980 | Moret et al. ............... 433/29 |
| 4,211,813 | A | 7/1980 | Gravisse et al. |
| 4,250,196 | A | 2/1981 | Friello |
| 4,292,329 | A | 9/1981 | Ogawa et al. |
| 4,316,915 | A | 2/1982 | Friello et al. |
| 4,466,983 | A | 8/1984 | Cifrese et al. |
| 4,479,781 | A | 10/1984 | Herold et al. |
| 4,504,502 | A | 3/1985 | Earle et al. |
| 4,513,012 | A | 4/1985 | Carroll et al. |
| 4,553,936 | A | 11/1985 | Wang |
| 4,624,594 | A | 11/1986 | Sasaki et al. |
| 4,629,583 | A | 12/1986 | Goguen |
| 4,642,235 | A | 2/1987 | Reed et al. |
| 4,647,450 | A | 3/1987 | Peters et al. |
| 4,661,070 | A | 4/1987 | Friedman |
| 4,683,138 | A | 7/1987 | Glass et al. |
| 4,693,684 | A | 9/1987 | Blatherwick et al. |
| 4,707,297 | A | 11/1987 | Paske, Jr. et al. |
| 4,773,785 | A | 9/1988 | Katz |
| 4,792,453 | A | 12/1988 | Reed et al. |
| 4,813,870 | A | 3/1989 | Pitzen et al. |
| 4,910,031 | A | 3/1990 | Budd et al. |
| 4,911,830 | A | 3/1990 | Bromley et al. |
| 4,913,919 | A | 4/1990 | Cornwell et al. |
| 4,952,143 | A | 8/1990 | Becker et al. |
| 4,975,288 | A | 12/1990 | Hager et al. |
| 4,980,178 | A | 12/1990 | Cherukuri et al. |
| 4,981,707 | A | 1/1991 | Morris |
| 4,983,381 | A | 1/1991 | Torres Zaragoza |
| 5,032,178 | A | 7/1991 | Cornell |
| 5,057,277 | A * | 10/1991 | Mauze et al. ............... 422/400 |
| 5,087,460 | A | 2/1992 | Cherukuri et al. |
| 5,125,819 | A | 6/1992 | Hager et al. |
| 5,208,010 | A | 5/1993 | Thaler |
| 5,248,508 | A | 9/1993 | Reed et al. |
| 5,267,859 | A * | 12/1993 | Discko, Jr. ............... 433/89 |
| 5,275,830 | A | 1/1994 | Smith |
| 5,275,831 | A | 1/1994 | Smith et al. |
| 5,298,268 | A | 3/1994 | Maegli |
| 5,316,473 | A | 5/1994 | Hare |
| 5,320,442 | A | 6/1994 | Yanagisawa et al. |
| 5,321,587 | A | 6/1994 | Fujita |
| 5,403,578 | A | 4/1995 | Gordon |
| 5,409,631 | A | 4/1995 | Fischer |
| 5,431,929 | A | 7/1995 | Yatka et al. |
| 5,445,608 | A | 8/1995 | Chen et al. |
| 5,464,651 | A | 11/1995 | Turk et al. |
| 5,487,662 | A | 1/1996 | Kipke et al. |
| 5,498,429 | A | 3/1996 | Orlandi et al. |
| 5,500,009 | A | 3/1996 | Mendes et al. |
| 5,569,477 | A | 10/1996 | Nesbitt |
| 5,571,152 | A | 11/1996 | Chen et al. |
| 5,578,089 | A | 11/1996 | Elsamaloty |
| 5,611,687 | A | 3/1997 | Wagner |
| 5,616,140 | A | 4/1997 | Prescott |
| 5,618,467 | A | 4/1997 | Turk et al. |
| 5,645,428 | A | 7/1997 | Yarborough |
| 5,702,432 | A | 12/1997 | Chen et al. |
| 5,713,738 | A | 2/1998 | Yarborough |
| 5,718,577 | A | 2/1998 | Oxman et al. |
| 5,736,175 | A | 4/1998 | Cea et al. |
| 5,783,108 | A | 7/1998 | MacKay |
| 5,785,527 | A | 7/1998 | Jensen et al. |
| 5,800,478 | A | 9/1998 | Chen et al. |
| 5,824,291 | A | 10/1998 | Howard |
| 5,827,002 | A | 10/1998 | Nakajima |
| 5,827,526 | A | 10/1998 | Dohnalek et al. |
| 5,829,976 | A | 11/1998 | Green |
| 5,834,002 | A | 11/1998 | Athanikar |
| 5,846,557 | A | 12/1998 | Eisenstadt et al. |
| 5,851,079 | A * | 12/1998 | Horstman ............ A45D 34/042 401/174 |
| 5,858,423 | A | 1/1999 | Yajima et al. |
| 5,866,179 | A | 2/1999 | Testa |
| 5,879,691 | A | 3/1999 | Sagel et al. |
| 5,879,694 | A | 3/1999 | Morrison et al. |
| 5,885,630 | A | 3/1999 | Zurawski et al. |
| 5,891,453 | A | 4/1999 | Sagel et al. |
| 5,894,017 | A | 4/1999 | Sagel et al. |
| 5,900,230 | A | 5/1999 | Cutler |
| 5,912,030 | A | 6/1999 | Huzinec et al. |
| 5,914,076 | A | 6/1999 | Schloss |
| 5,916,606 | A | 6/1999 | Record et al. |
| 5,922,347 | A | 7/1999 | Hausler et al. |
| 5,980,868 | A | 11/1999 | Homola et al. |
| 5,989,245 | A | 11/1999 | Prescott |
| 5,989,569 | A | 11/1999 | Dirksing et al. |
| 6,036,493 | A | 3/2000 | Sharma |
| 6,036,494 | A | 3/2000 | Cohen |
| 6,045,811 | A | 4/2000 | Dirksing et al. |
| 6,056,548 | A | 5/2000 | Neuberger et al. |
| 6,066,329 | A | 5/2000 | Morrison et al. |
| 6,077,073 | A | 6/2000 | Jacob |
| 6,083,002 | A | 7/2000 | Martin et al. |
| 6,102,705 | A | 8/2000 | Darnell |
| 6,106,293 | A | 8/2000 | Wiesel |
| 6,116,900 | A | 9/2000 | Ostler |
| 6,126,443 | A | 10/2000 | Burgio |
| 6,149,895 | A | 11/2000 | Kutsch |
| 6,155,735 | A | 12/2000 | Nakajima |
| 6,155,832 | A | 12/2000 | Wiesel |
| 6,156,028 | A | 12/2000 | Prescott |
| 6,162,055 | A | 12/2000 | Montgomery et al. |
| 6,227,739 | B1 | 5/2001 | Kageyama |
| 6,231,343 | B1 | 5/2001 | Ishibashi et al. |
| 6,254,388 | B1 | 7/2001 | Yarborough |
| 6,254,391 | B1 | 7/2001 | Darnell |
| 6,277,458 | B1 | 8/2001 | Dirksing et al. |
| 6,284,291 | B1 | 9/2001 | Siecke et al. |
| 6,287,120 | B1 | 9/2001 | Wiesel |
| 6,299,441 | B1 | 10/2001 | Novak |
| 6,306,370 | B1 | 10/2001 | Jensen et al. |
| 6,309,625 | B1 | 10/2001 | Jensen et al. |
| 6,312,666 | B1 | 11/2001 | Oxman et al. |
| 6,319,507 | B1 | 11/2001 | Delrieu et al. |
| 6,340,301 | B2 | 1/2002 | Darnell |
| 6,343,932 | B1 | 2/2002 | Wiesel |
| 6,343,933 | B1 | 2/2002 | Montgomery et al. |
| 6,354,837 | B1 | 3/2002 | Jensen |
| 6,358,339 | B1 | 3/2002 | Hiskey et al. |
| 6,361,320 | B2 | 3/2002 | Yarborough |
| 6,368,109 | B2 | 4/2002 | Lindquist |
| 6,368,576 | B1 | 4/2002 | Jensen et al. |
| 6,375,864 | B1 | 4/2002 | Phillips et al. |
| 6,382,979 | B2 | 5/2002 | Lindquist |
| 6,387,353 | B1 | 5/2002 | Jensen et al. |
| 6,416,319 | B1 | 7/2002 | Cipolla |
| 6,419,906 | B1 | 7/2002 | Xu et al. |
| 6,423,306 | B2 | 7/2002 | Caes et al. |
| 6,435,873 | B1 | 8/2002 | Burgio |
| 6,458,340 | B1 | 10/2002 | Ibsen et al. |
| 6,458,380 | B1 | 10/2002 | Leaderman |
| 6,530,709 | B1 | 3/2003 | Washington |
| 6,616,447 | B1 | 9/2003 | Rizoiu et al. |
| 6,623,272 | B2 | 9/2003 | Clemans |
| 6,652,839 | B2 | 11/2003 | Barreca |
| 2002/0070247 | A1 | 6/2002 | Kageyama et al. |
| 2002/0094506 | A1 | 7/2002 | Fischer et al. |
| 2004/0010299 | A1 * | 1/2004 | Tolkoff et al. ............... 607/88 |
| 2004/0146836 | A1 * | 7/2004 | Andersen ............ A61C 5/00 433/215 |
| 2005/0008584 | A1 | 1/2005 | Montgomery |

* cited by examiner

FIG - 1
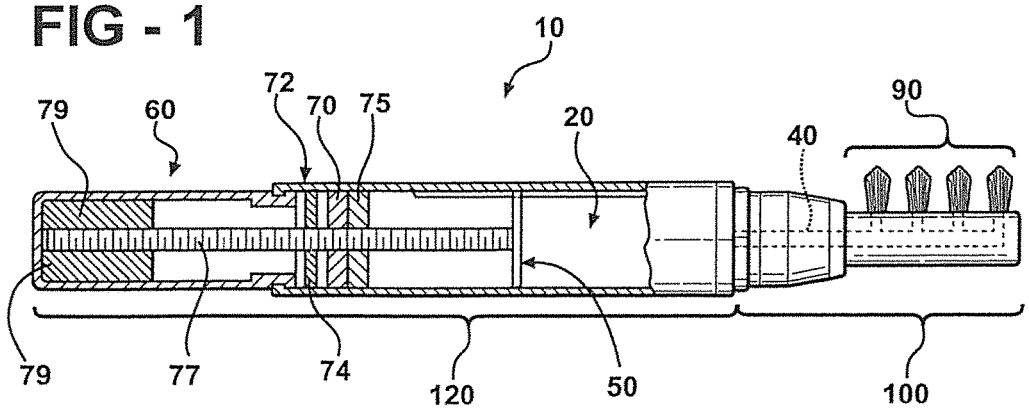
FIG - 1A
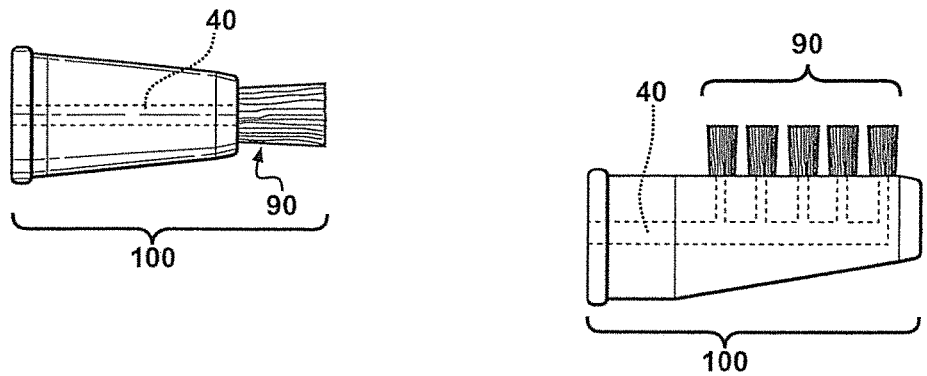
FIG - 1B
FIG - 1C
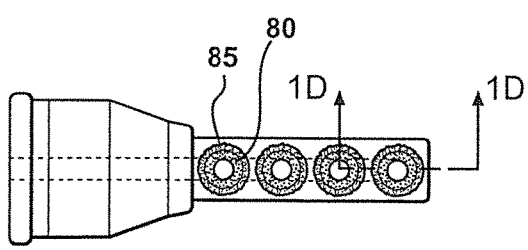
FIG - 1D
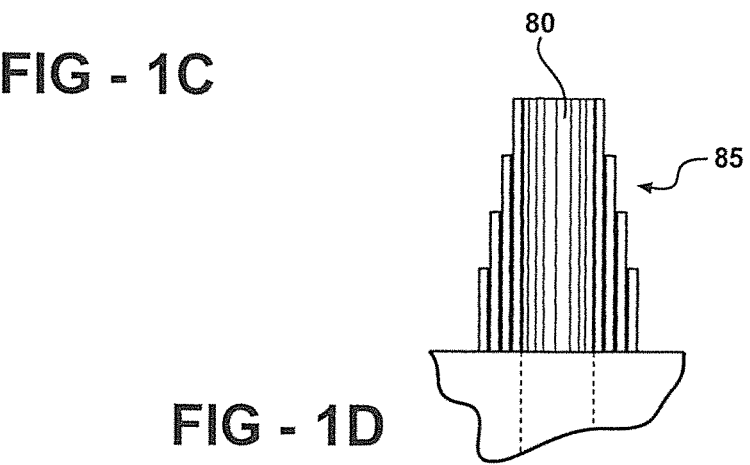

FIG - 7
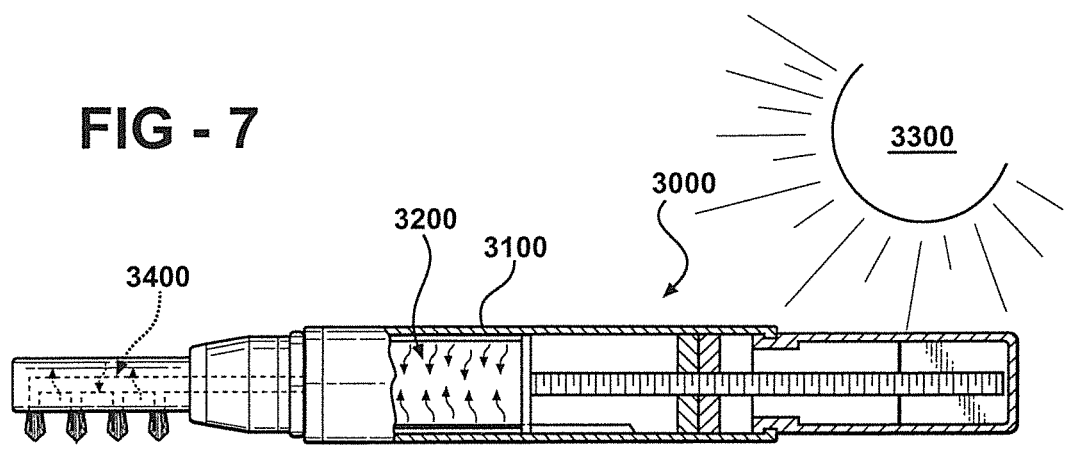
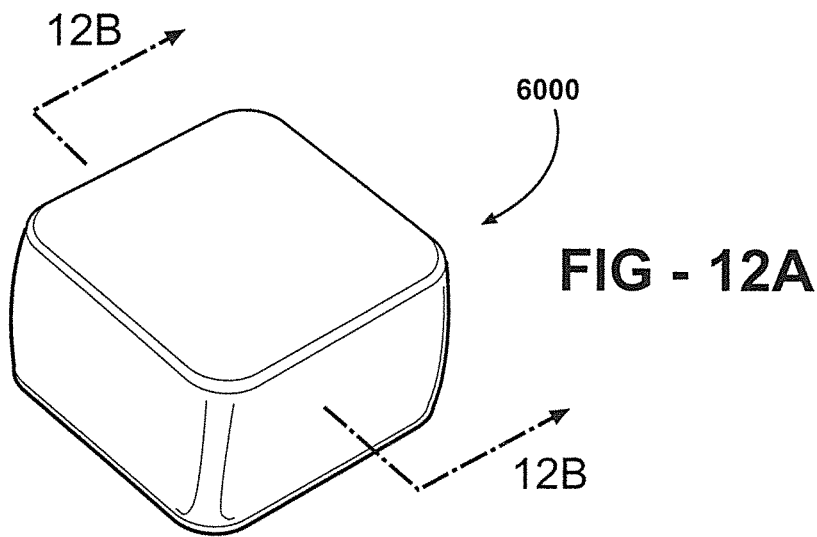
FIG - 12A
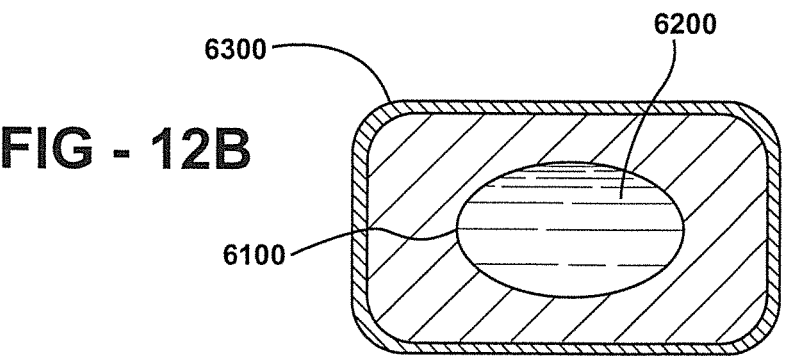
FIG - 12B

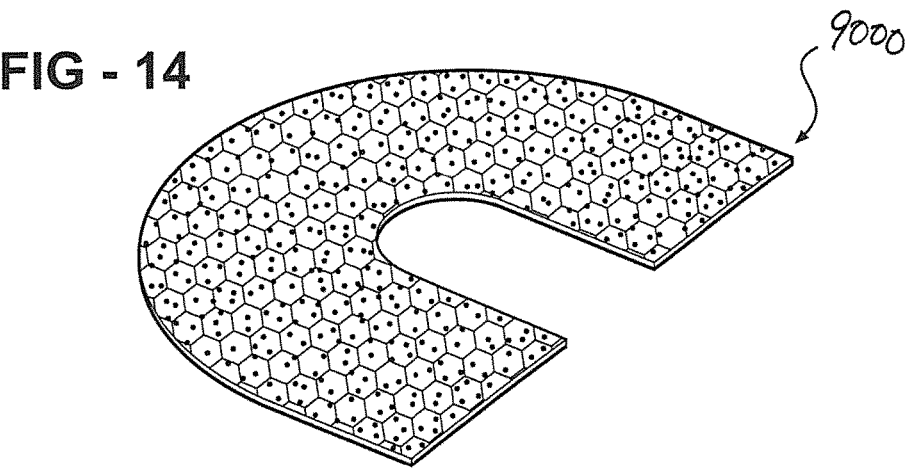
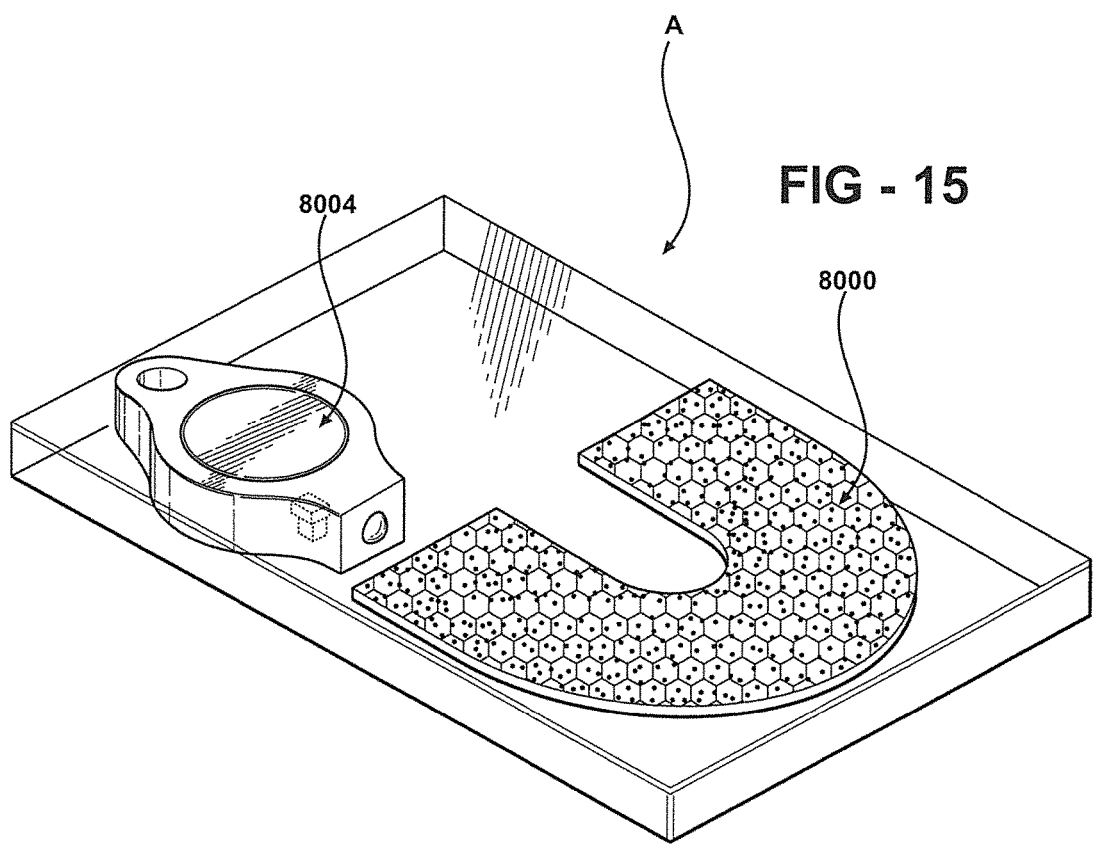

PROCESS OF TOOTH WHITENING AND APPARATUS THEREFOR

REFERENCE TO RELATED APPLICATIONS

This application is a divisional of U.S. patent application Ser. No. 10/872,256, filed Jun. 18, 2004, now U.S. Pat. No. 8,602,774, which claims priority from U.S. Provisional Patent Application Ser. No. 60/479,801, filed Jun. 19, 2003. U.S. patent application Ser. No. 10/872,256 is also a continuation-in-part of U.S. patent application Ser. No. 10/309,831, filed Dec. 4, 2002, now U.S. Pat. No. 7,645,137. The entire content of each application is incorporated herein by reference.

FIELD OF THE INVENTION

This invention relates to methods for whitening a user's tooth. In particular, the invention relates to methods and apparatus for more efficiently applying a tooth whitening composition and whitening a user's tooth.

BACKGROUND OF THE INVENTION

Dental bleaching is an increasingly popular treatment and dentists are searching for techniques that are both convenient and comfortable for their patients. Numerous methods and tools have been developed for the purpose of dental bleaching. Typically, a composition containing hydrogen peroxide is applied to the teeth and allowed to remain in contact with the tooth to be bleached. Various methods and devices have been developed to allow a user to apply a whitening composition to a tooth to be whitened. However, inexperienced or careless users may apply an excessive amount of whitening composition, with the result that the excess must be removed and discarded, wasting time and material. Worse yet, the excessive material may irritate gums or other tissues not intended to be in contact with large amounts of whitening composition. Thus, there exists a need for methods and apparatus for tooth whitening that provide more control over the delivery of whitening composition to a tooth.

SUMMARY OF THE INVENTION

A process of whitening a tooth provided by the invention includes the steps of providing a delivery device for mechanical dispensing of a predetermined amount of a whitening composition to an applicator tip; dispensing the amount of whitening composition to the applicator tip; applying the amount of whitening composition disposed on the applicator tip to the tooth to be whitened; and allowing the whitening composition to remain in contact with the tooth for a period of time sufficient to whiten the tooth. Optionally, the process further includes the step of exposing the whitening composition to light. The whitening composition is exposed to light before or after applying the amount of whitening composition disposed on the applicator tip to the tooth to be whitened. Optionally included is the step of exposing the whitening composition to light emitted from a light source disposed on the mechanical dispensing device. Another option is exposure of the whitening composition to light emitted from a light source disposed in the whitening composition.

Another optional step of an inventive process includes providing a dental apparatus, the dental apparatus having a support structure adapted to be placed entirely within a user's mouth; and a light source disposed on or in the support structure such that light emitted from the source impinges on the dental whitening composition on the tooth to be whitened, wherein the apparatus has a preferred volume between 0.5-450 cm$^3$. Optionally, the dental apparatus includes a support structure which is moldable to conform to the user's dentition.

Also provided is an inventive device having a reservoir containing a tooth whitening composition, the device adapted to mechanically dispense a predetermined amount of a tooth whitening composition to an applicator tip. Optionally, the device includes a light source disposed on or in the device such that light emitted by the light source impinges on the tooth whitening composition. In other optional configurations, the light source is disposed on a wall of the reservoir, a wall of the applicator tip, and/or on a cap which is adapted to cover the applicator tip. A light source includes a light emitting diode, a laser diode, a luminescent material disposed in the reservoir, a luminescent material disposed in and/or on a wall of the reservoir.

Further detailed is chewing gum or candy composition which includes a confectionary base and a tooth whitening composition. Optionally, the confectionary base is a chewing gum base which includes an ingredient selected from the group consisting of: a natural or synthetic elastomer, a solvent, an emulsifying agent, a filler, a flavoring agent, a coloring agent, a preserving agent and a sweetening agent. Further optionally, the confectionary base is a candy base comprising an ingredient selected from the group consisting of: a solvent, an emulsifying agent, a filler, a flavoring agent, a coloring agent, a preserving agent and a sweetening agent. Preferably, the whitening composition is present in an amount ranging from 1-50% by weight and includes a peroxide. Optionally, the peroxide is present at a concentration ranging from 5-35%.

In a further option, an inventive chewing gum or candy includes a light source. In one embodiment the light source is selected from the group consisting of: phosphorescent, fluorescent, chemiluminescent and a combination thereof. Also optionally, the light source is a microencapsulated chemiluminescent light source.

In addition, chewing gum or candy composition is provided which includes a confectionary base configured to form a wall enclosing a cavity and a tooth whitening composition disposed in the cavity. Where the confectionary base is a chewing gum base it may include a natural or synthetic elastomer, a solvent, an emulsifying agent, a filler, a flavoring agent, a coloring agent and a sweetening agent. Where the confectionary base is a candy base it may include a solvent, an emulsifying agent, a filler, a flavoring agent, a coloring agent and a sweetening agent. The included whitening composition is optionally in the form of a liquid, gel, microencapsulated liquid and/or microencapsulated gel. Optionally, the whitening composition is present in an amount ranging from 1-50% by weight and includes a peroxide. Further optionally, the peroxide is present at a concentration ranging from 5-35%. An included whitening composition optionally has a solvent, an emulsifier, a buffering agent, a flavoring agent, a sweetener, a coloring agent a thickener, and/or a preservative included therein.

An inventive chewing gum optionally includes an external coating and in a further option, may include a light source. Preferred are phosphorescent, fluorescent and chemiluminescent light sources, and particularly a microencapsulated chemiluminescent light source.

Another embodiment of the invention is a commercial package including a mechanical dispensing device adapted to mechanically dispense a predetermined amount of a whitening composition. Instructions for use are also included in the package. Optionally included in the package is a separator for separating a user's cheeks, gums or tongue from contact with teeth being whitened. Also optionally included is a dental apparatus moldable at the time of use to form a dental tray custom fit to a user's teeth, the apparatus including a support structure and a light source. The support structure may be a sheet material having a textured surface, optionally including a reservoir. In one option, the light source is integral to the support structure.

Also provided is a process for tooth whitening which includes the steps of providing a chewing gum or candy tooth whitening composition delivery vehicle which has a confectionary base and a tooth whitening composition, to a user, contacting the user's teeth with whitening composition and allowing the whitening composition to remain in contact with the teeth for a period of time sufficient to whiten them. Optionally, these steps are repeated a number of times in order to achieve a desired level of whitening, the number of times ranging from about 2-100. In another optional step, the whitening composition is exposed to light prior to the step of contacting a tooth of the user with the composition. Also, the whitening composition may be exposed to light during and/or after the step of contacting a tooth of the user with the composition.

BRIEF DESCRIPTION OF THE DRAWINGS

FIG. 1 is a drawing illustrating a delivery device according to the invention;
FIG. 1A is a drawing illustrating a tip portion of a delivery device according to the invention;
FIG. 1B is a drawing illustrating a tip portion of a delivery device according to the invention;
FIG. 1C is a drawing illustrating a tip portion of a delivery device according to the invention;
FIG. 1D is a drawing illustrating a tip portion of a delivery device according to the invention;
FIG. 7 is a drawing illustrating another inventive delivery device;
FIG. 12A is a drawing illustrating a gum or candy delivery device according to the invention;
FIG. 12B is a drawing illustrating a gum or candy delivery device according to the invention;
FIG. 14 is a drawing illustrating an embodiment of an inventive apparatus;
and
FIG. 15 is a drawing illustrating an embodiment of an inventive commercial package.

DETAILED DESCRIPTION OF THE INVENTION

Figure 2:
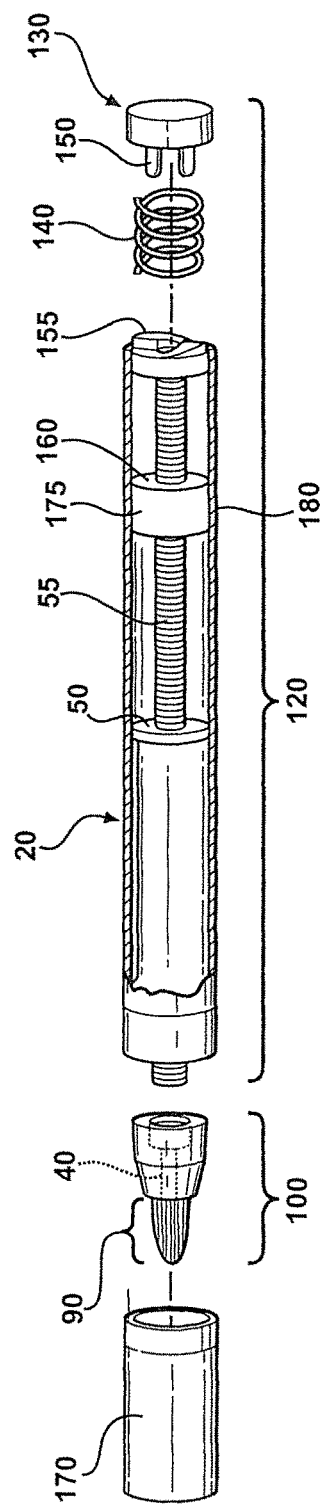
FIG. 2 is a drawing illustrating an alternative delivery device.

An inventive device adapted to mechanically dispense a predetermined amount from a reservoir containing a tooth whitening composition is described below.

Mechanical Dispensing Device

A delivery device used in an inventive method is adapted to mechanically dispense a whitening composition. Although devices adapted to mechanically dispense a substance are known in the art, they have not been loaded to dispense a tooth whitening composition.

An inventive device includes a user activation of a mechanism for moving a desired amount of a substance out of a reservoir and onto an applicator tip for application to a tooth. User activation of a mechanical dispenser includes activation by push-button, twist-turn, lever and the like. In a preferred embodiment, the desired amount may be predetermined such that the user dispenses a known amount with each activation of the push-button, twist-turn, lever and the like.

A generalized delivery device of the type used in an inventive method is shown in FIG. 1. An assembled delivery device exemplary of a twist-turn activated mechanism is shown at 10. A delivery device includes a reservoir 20 for holding a whitening material to be delivered. An exemplary user activated unidirectional twist-turn mechanism is shown. To activate the mechanism, a user rotates the handle portion 60 moving the expelling platform 50 incrementally through the reservoir 20 toward the tip portion 100. In the specific embodiment shown in FIG. 1, a ratchet piece 70 fits in a complementary piece 75 such that twist-turn action of the handle is unidirectional and advancement of the shaft is incremental. A spring 74 is present which buffers the movement of the ratchet piece 70 as it moves against the complementary piece 75. Piece 75 is fixed to wall 72 of the device.

Shaft 77 and piece 75 are in threaded connection such that rotation of shaft 77 results in its advancement through piece 75. Shaft 77 includes lateral grooves (not shown) which slidably interact with projections 79. The projections 79 are fixed to the handle 60. Thus, turning the handle 60 causes the shaft 77 to turn. Further, turning the shaft 77 and handle 60 causes movement of the shaft which is attached to platform 50. This incremental movement of expelling platform 50 pushes a predetermined amount of whitening composition into tip portion 100. The predetermined amount is proportional to the extent of the incremental movement.

Tip portion 100 may be attachable to a body portion 120 or integrally formed with the body portion. The tip portion 100 may be connected to the body portion by methods such as by interlocking threaded engagement, snap fit engagement or the like. As depicted in FIGS. 1, 1A and 1B, tip portion 100 includes a flow tube 40 through which whitening composition moves towards applicator tip 90. The flow tube optionally extends into the applicator tip 90. As shown in FIGS. 1C and 1D, applicator 90 is preferably a brush which may have brush bristles 80 having nearly uniform length and/or flow bristles 85 having a graduated bristle length.

A second exemplary delivery device is shown in FIG. 2. A reservoir 20 is shown for storing whitening composition which is dispensed by user engagement of a push button activator 130. The push button activator 130 is shown in contact with a spring 140. Activation of push button activator 130 causes engagement of notched pieces 150 and 155 which engagement rotates shaft casing 160 which is fixed to piece 155. Shaft 55 includes lateral grooves (not shown) which slidably interact with projections fixed on shaft casing 160. Thus, rotation of piece 155 causes the shaft 55 to turn. Shaft 55 is in threaded engagement with piece 175 which is fixed to wall 180. Further, turning the shaft 55 movement of platform 50 an incremental distance towards the tip portion 100. This incremental movement of expelling platform 50 pushes a predetermined amount of whitening composition into tip portion 100. The predetermined amount is proportional to the extent of the incremental movement. Optionally, a delivery device includes a cap 170 which fits over an applicator 90 or tip portion 100.

Figure 3:
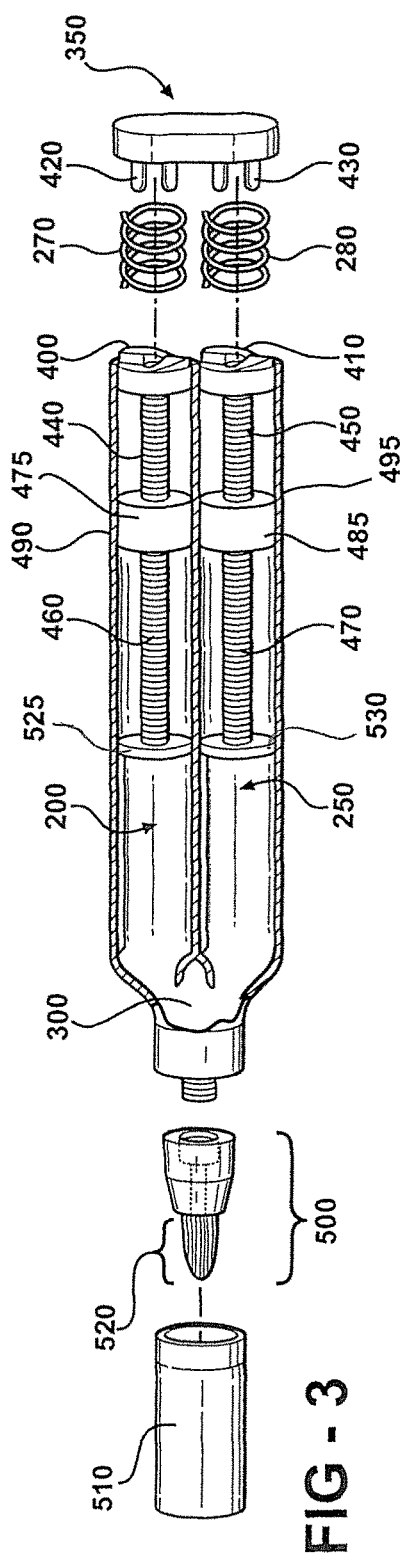
FIG. 3 is a drawing illustrating a different delivery device.

An alternative delivery device has two reservoirs. As shown in FIG. 3, a first reservoir 200 and a second reservoir 250 may be filled with whitening composition components which combine in mixing area 300. In this example, whitening composition components are moved forward by user engagement of a push button activator 350. The push button activator 350 shown contacts a first spring 270 and a second spring 280. Activation of push button activator 350 causes engagement of notched pieces 400 and 410 with notched pieces 420 and 430 respectively. This engagement rotates shaft casings 440 and 450 which are fixed to pieces 400 and 410 respectively. Shafts 460 and 470 include lateral grooves (not shown) which slidably interact with projections fixed on shaft casings 440 and 450. Thus, rotation of pieces 400 and 410 cause the shafts 460 and 470 to turn. Shafts 460 and 470 are in threaded engagement with pieces 475 and 485 respectively which are fixed to wall 490 and 495 respectively. Further, turning the shafts 460 and 470 causes movement of platforms 525 and 530 an incremental distance towards the tip portion 100. This incremental movement of platforms 525 and 530 pushes a predetermined amount of whitening composition into tip portion 500. The predetermined amount is proportional to the extent of the incremental movement. Optionally, a delivery device includes a cap 510 which fits over an applicator 520 or tip portion 500. It is recognized that the distance between threads on shafts 460 and 470 may be independently chosen such that different amounts of compositions in reservoirs 200 and 250 may be dispensed into the mixing area 300.

Figure 4:
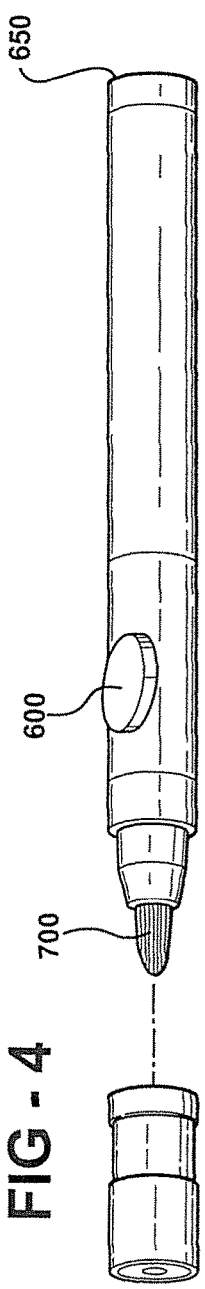
FIG. 4 is a drawing illustrating a delivery device according to the invention.

FIG. 4 illustrates another type of delivery device for mechanical dispensing of a predetermined amount. In particular this figure illustrates an alternative arrangement of a user activated button 600. This examples depicts an embodiment in which the user activated button, lever or the like is positioned between a proximal end of the device 650 and a distal applicator tip end 700. Further examples of delivery devices include those described in U.S. Pat. Nos. 5,851,079; 5,320,442; 4,813,870; 4,773, 785; 6,530,709; 4,624,594; 5,827,002; 6,155,735; 6,083,002; 4,043,042; 4,479,781; 4,693,684; 5,829,976 and in US Patent Application No. 2002/0094506.

In some embodiments, parts of the delivery device, in particular the reservoir portion, may be made of material that limits light exposure of a whitening composition contained therein. However, it will be noted that in some applications, such as those where the whitening composition is exposed to light in order to activate a component of the composition, the device or a portion of the device, such as a reservoir wall, tip portion wall or cap wall, is made of material transparent or translucent to the activating light.

Whitening Compositions

The dental whitening composition preferably includes an oxidizing agent. Oxidizing agents used in dental whitening include, for example, a peroxide, an alkali metal percarbonate, an alkali metal perborate or a combination thereof are illustrative of useful oxidizing agents. Most commonly used peroxides include hydrogen peroxide, carbamide peroxide and alkali metal peroxides.

Concentrations of oxidizing agents applicable in dental whitening depend on the circumstances of use. Exemplary concentrations are detailed in, for example, U.S. Pat. Nos. 5,032,178; 5,409,631; 5,785,527; 6,149,895; 6,155,832; 6,162,055; 6,165,448; 6,231,343; 6,306,370; 6,309,625; 6,312,666; 6,343,933; 6,387,353; 6,440,396; and 6,458,340. A peroxide is typically used at concentrations ranging from 1% to 50%. Typically, lower concentrations of hydrogen peroxide, from 2-10% are made available to patients for in home use. Higher concentrations are used in a clinician's office, ranging from 10-35 percent.

The dental whitening composition may further include optional ingredients such as a buffer, a thickener or gelling agent, a solvent, a surfactant, additives such as flavoring agents or preservatives and other inert customary ingredients as detailed in, for example, U.S. Patents referenced above. A further ingredient of the dental whitening composition is an optional heat or light absorbing component or a reaction accelerator such as a catalyst as detailed in, for example, U.S. Pat. Nos. 6,287,120; 6,439,888 and 6,440,396.

A whitening composition may also contain a therapeutic agent such as an agent to treat dental or systemic diseases or conditions, including anti-plaque agents, anesthetics, desensitizing agents, analgesics, antibiotics, antifungals, antimicrobials, antivirals, anti-inflammatory agents, steroids, remineralizing agents, and anticariogenic agents.

In another embodiment of the invention, a whitening composition may include ascorbic acid as a whitening agent. Ascorbic acid may be present in amounts ranging from 1-50% by weight of the whitening composition.

In some cases a whitening composition may be stored in multiple component form. For example, a first component which is a carbamide preparation may be stored separately from a second component such as an aqueous solution in order to inhibit breakdown of the carbamide during storage. Just prior to use, the two components are mixed to produce a whitening composition for application to a tooth. Other whitening compositions formed by mixing of components just prior to application to a tooth are exemplified in U.S. Pat. Nos. 6,290,935; 6,149,855; and 5,648,064.

The dental whitening composition may assume any of various forms, illustratively including liquid, gel, emulsion, putty or paste. The composition may further be in a microencapsulated form such as alginate beads or agar gel beads, liposomes, niosomes, or other form in which a boundary layer is formed to surround the whitening composition. Such formulations are exemplified in U.S. Pat. Nos. 6,375,985; 6375,968; 6,319,507; 6,217,908 and Microencapsulation: Methods and Industrial Applications in Drugs and the Pharmaceutical Sciences, Vol. 73; S. Benita (Ed.); Marcel Dekker; 1996. A time-release formulation is also contemplated, such as that disclosed in U.S. Pat. No. 6,197,331, for example. Further examples of whitening compositions, formulations and devices are included in patent application Ser. No. 10/309,831 which is hereby incorporated by reference.

A presently preferred whitening composition comprises a gel containing 12% hydrogen peroxide, glycerin, propylene glycol, silica, carbopol, EDTA, ammonium hydroxide and flavoring.

Light and Tooth Whitening

A whitening composition included in an inventive apparatus and method may be used in conjunction with a light source for accelerating the tooth whitening. Light is used to activate a whitening composition before or after application to a tooth to be whitened. Advantageously, a light source is included on or in a dispensing device according to the invention. Further, an apparatus including a light source is provided by the present invention which may be placed entirely within the mouth of a user in a process of whitening a tooth.

A light source may be a luminescent source, such as fluorescent, phosphorescent or chemiluminescent. Other exemplary light sources include light emitting diodes and laser diodes. Light sources operable in activating whitening are those emitting light between about 300-1000 nanometers. In particular, a light source emitting light having a wavelength of about 300-500 nanometers is preferred, and especially preferred is a light source emitting light having a wavelength of about 390-430 nanometers. Further preferred is a light source emitting light having a wavelength of 400-410 nanometers.

Time of exposure necessary to activate a whitening composition depends on the particular light source and whitening composition used. Generally, a time sufficient to activate a whitening composition ranges between about 1 second to about 1 hour, but may be more or less depending on the specific light source and whitening composition.

Light sources and wavelengths of light providing energy that promotes activation of dental whitening compositions, as well as exposure times, are exemplified in U.S. Pat. Nos. 4,661,070; 4,952,143; 5,032,178; 5,658,148; 5,713,738; 5,785,527; 6,056,548; 6,106,293; 6,149,895; 6,155,832; 6,162,055; 6,231,343; 6,287,120; 6,361,320; 6,416,319.

Light Source Disposed on or in a Dispensing Device

Figure 5:
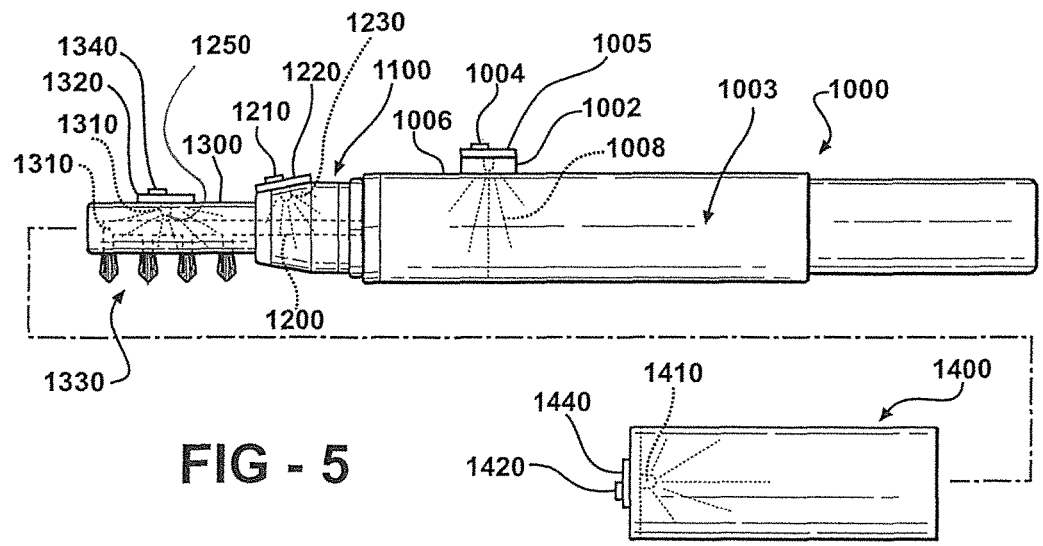
FIG. 5 is a drawing illustrating a delivery device according to the invention.

In one embodiment of an inventive device, a light source is disposed on the mechanical dispensing device such that light emitted from the light source impinges on the whitening composition. For example, a light source may be disposed on the mechanical dispensing device such that light emitted from the light source impinges on whitening composition in a reservoir of the device and/or which has been dispensed onto the applicator tip. As depicted in FIG. 5 a dispensing device 1000 includes a light source 1002 disposed on a wall 1006 adjacent a reservoir 1003 containing a whitening composition. Light 1008 from the light source 1002 impinges on whitening composition in the reservoir 1003. An on/off switch 1004 is depicted along with a battery 1005.

In a further embodiment, a light source disposed on an inventive device is configured such that light emitted from the light source may be directed toward a tooth. (not shown) Thus, the whitening composition may be activated before application by exposure to light in the device or on the applicator tip, and/or after application to the tooth to be treated.

Diode Light Source Disposed on or in a Dispensing Device

In one embodiment, a light source disposed on a mechanical dispensing device is a light emitting diode or laser diode. Diode light sources of various types are preferred, including those emitting light between about 300-1000 nanometers. In particular, a diode light source emitting light having a wavelength of about 300-500 nanometers is preferred, and especially preferred is a diode light source emitting light having a wavelength of about 390-430 nanometers. Further preferred is a diode light source emitting light having a wavelength of 400-410 nanometers.

Figure 5A:
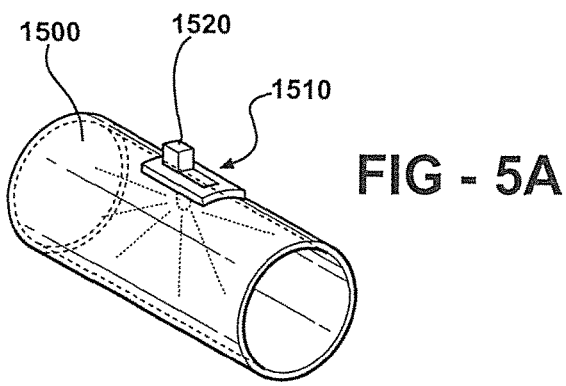
FIG. 5A is a drawing illustrating a cap of delivery device according to the invention.

Particularly preferred is a diode light source, especially an LED, disposed on the mechanical dispensing device such that light emitted from the light source impinges on whitening composition which has been dispensed onto the applicator tip. For example, an LED may be disposed on an internal or external surface of a cap, the cap positionable over the applicator tip. As shown in FIGS. 5 and 5A, caps 1400 and 1500 include a light source 1410 positioned on the cap such that light emitted from the light source impinges on whitening composition dispensed on the applicator tip or in the flow tube. On/off switches 1420 and 1520 are shown. In addition batteries 1440 and 1510 are depicted.

Further, an LED may be disposed such that light emitted from the LED impinges on whitening composition in the reservoir or flow tube. For instance, an LED may be positioned adjacent the reservoir or flow tube, such as on an internal or external surface of the device adjacent the reservoir or on an internal or external surface of the tip portion. As shown in FIG. 5, a light source attached to a power source and having an on/off switch is positioned on a dispensing device. A light source 1250 includes an LED 1230, a battery 1220 and an on/off switch 1210. The light source 1250 is positioned adjacent the flow tube 1200 on wall 1100 such that light emitted from the LED impinges on whitening composition in the flow tube. Further depicted is an LED 1310, a battery 1320, a switch 1340 disposed on wall 1300 adjacent the flow tube 1200 in the applicator tip 1330. In an embodiment where the light source is positioned on an external surface of a component of an inventive mechanical dispensing device, the surface transmits the light emitted by the light source, or a portion thereof, through the surface to impinge on the whitening composition. Further, a flow tube is transparent or translucent to light emitted by the light source, or a portion thereof, such that light impinges on the whitening composition disposed therein.

A light source disposed on the mechanical dispensing device is preferably powered by an energy storage device such, as a battery or capacitor, incorporated into the device. Alternatively, a light source on an inventive device may be connected to an external power source. The light source is turned on by a conventional on/off switch, push button activator, or the like. An inventive device may include one or more switch operated light sources. Where multiple light sources are included, they may be configured such that each may be activated separately, all at once, or in various combinations.

A preferred LED source is less than 1.75 inches long, less than 1 inch in width and less than ⅜ inch in depth.

Luminescent Material Light Source Disposed on or in a Dispensing Device

In another embodiment, a luminescent material is included on and/or in a mechanical dispensing device such that light emitted from the luminescent material impinges on whitening composition in the reservoir, flow tube, or applicator tip. For example, a luminescent material may be integral to the dispensing device, being included in a wall or other structural aspect of the device.

In one embodiment, a luminescent material which is included in a component of the device includes a phosphorescent material. Phosphorescent materials are those which are excited by UV or visible light, resulting in the emission of light that lasts after the exposure to the exciting light has ceased. Duration of the emission is typically from minutes to hours, but can even extend for several days. Many useful phosphorescent materials occur naturally or have been developed, including both inorganic and organic compounds.

Common inorganic phosphorescent materials suitable for use as a light source in the present invention include a metal cation, a non-metal anion and an "activator". Examples of suitable inorganic phosphors include sulfides, metal aluminate oxides, silicates and various rare earth compounds. For instance, ZnS and ZnS may be combined with various activators such as aluminum, cerium, copper, europium, gadolinium, gallium, gold, indium, lead, manganese, praseodymium, samarium, scandium, silver, terbium, and other rare earth elements and halogens to produce a phosphorescent material, and these may be used as a light source in the invention. Further examples of sulfide phosphors illustratively include alpha barium-zinc sulfides, barium-zinc-cadmium sulfides, CaS:Bi, CaSrS:Bi, strontium sulfides, ZnCdS:Cu and ZnCdS:Ag. Metal aluminate oxides include alkaline earth aluminate oxides, such as strontium aluminum oxide, calcium aluminum oxide and barium aluminum oxide. Strontium aluminate with a europium activator ($SrAlO_3$:Eu) is an exemplary phosphorescent material suitable for use as a light source in an inventive apparatus. Further oxide phosphorescent materials that illustrate phosphorescent materials that may be used as a light source in the invention include aluminum oxides, boric oxides, calcium oxides, dysprosium oxides, europium oxides and strontium oxides. Further examples of phosphorescent materials include those taught in U.S. Pat. Nos. 3,595,804; 3,957,678; 3,970,582, 5,376,303, 5,424,006, 5,558,817 and 5,853,614. Examples of phosphorescent organic materials are found in U.S. Pat. Nos. 5,229,16 and 5,618,467. Any of these listed phosphorescent materials, mixtures thereof, and art recognized equivalents may be used as a light source in an apparatus according to the present invention.

Preferred phosphorescent light sources are those having long-lasting light emission. For example, a particularly preferred light source is strontium aluminate with a europium activator ($SrAlO_3$:Eu) is a preferred long-lasting emitter, having an emission time of about 10 hours following exposure to exciting light.

Phosphorescent materials suitable for use in an inventive apparatus are commercially available, illustratively including those manufactured and sold under the brand name Picariko by Chemitech, Inc., Tokyo and available from F. W. Bass International; those made by Nemoto & Company, Tokyo and available from United Mineral & Chemical Corporation, Lyndhurst, N.J. under the brand name LumiNova. Further, PermaglowR products by Chemitech Inc., Tokyo such as Natural Blue color, having a peak emission at 489. A preferred phosphorescent material is in the form of particles having 30-65 micron size, especially 45-65 micron size, since particles in this range produce a desired intensity of light. In some embodiments, preferred phosphorescent materials are particles having grain size in the range of 5-200 microns and, more preferably ranging between 10-100 microns. Also, a preferred material has a particle size in the range of 200-180 mesh International Standards. A mesh of 125 American Standard is also useful.

In an embodiment of the present invention, a phosphorescent material is included in a structure of a dispensing device. For example, a phosphorescent material is included in a wall of a reservoir of an inventive device such that light emitted by the phosphorescent material impinges on whitening composition in the reservoir. As shown in FIG. 7, a device 3000 includes a phosphorescent material in a wall 3100 adjacent the reservoir 3200 containing a whitening composition. The material is exposed to a light 3300 resulting in emission of light from the wall into the reservoir. A light source may also be disposed on the device in order to excite the luminescent material included in the wall (not shown). Optionally, the phosphorescent material is incorporated in a select portion of the wall such that whitening composition in a reservoir 3400 proximal to the applicator tip is preferentially exposed to the light. In a further option, the phosphorescent material is incorporated in a select portion of the wall such that whitening composition on the applicator tip is preferentially exposed to the light.

In a particularly preferred embodiment, a phosphorescent material is included in or on the dispensing device along with a diode source such that the diode light source emits light having a wavelength which excites the phosphorescent material.

Fluorescent Light Sources

A fluorescent source may be included in an inventive device. For example, a fluorescent material is included in a wall of a reservoir of an inventive device such that light emitted by the fluorescent material impinges on whitening composition in the reservoir. Optionally, the fluorescent material is incorporated in a select portion of the wall such that whitening composition in a reservoir proximal to the applicator tip is preferentially exposed to the light. In a further option, the fluorescent material is incorporated in a select portion of the wall such that whitening composition on the applicator tip is preferentially exposed to the light. Fluorescent light sources suitable for use in an inventive apparatus illustratively include such compounds as the commercially available coumarin dyes such as Fluorescent Yellow FP, Macrolex Fluorescent Yellow 10GN, and Fluorescent Red G, (Bayer); Thermoplast Yellow 084 (BASF), and Solvent Orange 63, HOSTASOL Solvent Yellow 98, and Vat Red 41, (Clariant Corp.) and LUMOGEN F Dyes manufactured by BASF Corporation as well as art recognized equivalents.

Methods and compositions for forming luminescent articles by including a luminescent material in a resin, plastic, wax, sheet material or other support structure forming material are exemplified in U.S. Pat. Nos. 3,796,668; 4,211,813; 4,629,583; 4,707,297; 4,911,830; 5,464,651; 5,618,467; 5,783,108; 5,914,076 and 6,375,864.

Chemiluminescent Light Sources

A chemiluminescent light source refers to light produced by a chemical reaction. Different colors of chemiluminescent light, illustratively including blue, green and yellow, are produced according to the different chemical reactants. Examples of chemiluminescent light reactants and systems are found in U.S. Pat. Nos. 3,391,068; 3,511,612; 3,539,794; 3,557,233; 3,576,987; 3,584,211; 3,597,362; 3,654,525; 3,749,620; 3,752,406; 3,775,336; 3,800,132; 3,808,414; 3,888,786; 3,940,604; 3,974,368; 4,064,428; 4,313,843; 4,751,616; and 4,717,511.

Components of one type of chemiluminescent reaction include an oxalate component, an activator component and a fluorophore. Illustrative examples of an oxalate component include a phenyl oxalate ester such as dibutyl phthalate, bis(2,4,5-trichloro-6-carbopentexyphenyl)oxalate, bis(2,4-dinitrophenyl)oxalate (DNPO) and bis(2,4,6-trichlorophenyl)oxalate. Illustrative examples of an activator include dimethyl phthalate, t-butyl alcohol, hydrogen peroxide and sodium salicylate. Examples of fluorophores used in chemiluminescent reactions include 1-chloro-9,10-bis(phenylethynyl)anthracene, 9,10-diphenylanthracene, Rhodamine B, 5,12-Bis(phenylethynyl)-naphthacene and tetraphenylnaphthacene. Further chemiluminescent systems may be based on dioxetanes, luminols, acridinium esters and aryloxalates, as described in H. Akhavan-Tafti, et al., Chemiluminescent Haloalkoxy-substituted Dioxetanes: Properties and Applications, in *Bioluminescence and Chemiluminescence Molecular Reporting with Photons*, J. W. Hastings, L. Kricka and P. Stanley, Eds., John Wiley and Sons, Chichester, 497-500 (1997) and Bioluminescence and Chemiluminescence: Progress and Current Applications Robinson by Phillip E. Stanley (Editor), Larry J. Kricka (Editor), World Scientific Pub Co; 2002. Other chemiluminescent light sources include bioluminescent systems such as those taught in U.S. Pat. No. 5,876,995.

Components of chemiluminescence reactions are provided in separate containers and the components combined when chemiluminescent light production is desired. Glow sticks and glow tubes are examples of available commercial packaging for chemiluminescent materials. Typically, such packaging includes a breakable multi-compartment internal container, each enclosing a chemical reactant or stable mixture of selected reactants. The internal containers are surrounded by an outer container such that by breaking the internal containers, the reactants are mixed and held within the outer container. For example, a phenyl oxalate ester and a fluorophore may be stored together in one compartment, and hydrogen peroxide in another compartment, the compartments broken in order to mix the reactants and produce light.

In another arrangement, an oxalate compound and a fluorophore may be stored together in one inner compartment, and a hydrogen peroxide containing composition is present within the outer container, such that the inner compartments broken in order to mix the reactants within the outer container and produce light. The contents of this container may then be applied to a support or tooth as a light source. Additionally, it will be appreciated that the hydrogen peroxide present in a light source of this type is also a whitening composition.

In an embodiment of a device according to the invention, compartmentalized chemiluminescent reactants are disposed on or in the device such that when a barrier between the compartments is broken, chemiluminescent light impinges on whitening composition disposed in the reservoir, flow tube, or on the applicator tip, for instance. In a further embodiment of the invention, a chemiluminescent reaction component is microencapsulated such that breaking of the microencapsulation barrier, for example by shaking, sonication, finger pressure after application to teeth, tearing of the microencapsulation barrier by mechanical stress as the microencapsulated material passes through a structure capable of tearing the barrier, such as a narrow neck structure, and the like, results in generation of light impinging on the whitening composition. For example, a microencapsulation barrier may be relatively easily broken where a gelatin microencapsulation component is used.

In one embodiment, a first component of a chemiluminescent reaction is disposed in the device and a second component is external to the device, for example, disposed on a tooth to be whitened, or on an apparatus, or the like.

Light Source in a Whitening Composition

Figure 6:
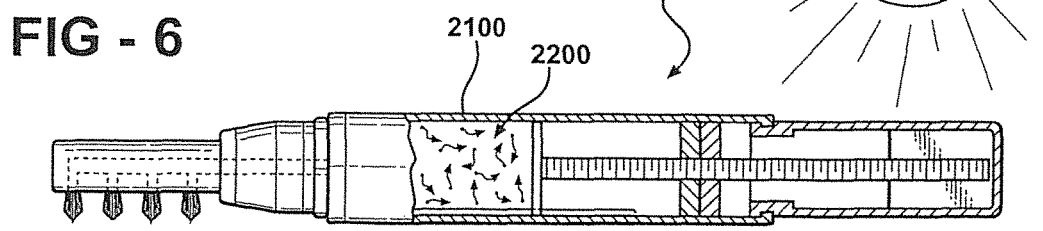
FIG. 6 is a drawing illustrating an inventive delivery device.

In an embodiment of the invention, a whitening composition includes a light source. For example, a luminescent substance is present in the whitening composition. The luminescent substance emits light which impinges on other components of the whitening composition. In one embodiment, as shown in FIG. 6, a dispensing device 2000 contains a microencapsulated phosphorescent material in a whitening composition 2200 in the reservoir 2100. In operation, the phosphorescent material is exposed to an exciting light source 2400. The excited material emits light which impinges on the whitening composition. Similarly, a fluorescent, or chemiluminescent material may be included in a whitening composition.

Intra-Oral Light Source

In an embodiment of the present invention, a dental apparatus including a light source, fitting entirely within the mouth, for use intra-orally to activate a whitening composition, is provided to a user.

An apparatus according to the present invention includes a support structure and a light source. The apparatus is adapted to be contained entirely within the closed mouth of a user, such that the apparatus operates to activate a whitening composition in the closed mouth of a user without any part of the apparatus protruding from the mouth. This allows the user to rest comfortably while receiving the benefits of dental whitening. FIGS. 1A and 2 illustrate embodiments of the apparatus 10 in place in a user's mouth.

Support Structure Included in an Apparatus

Form of a Support Structure

Figure 8A:
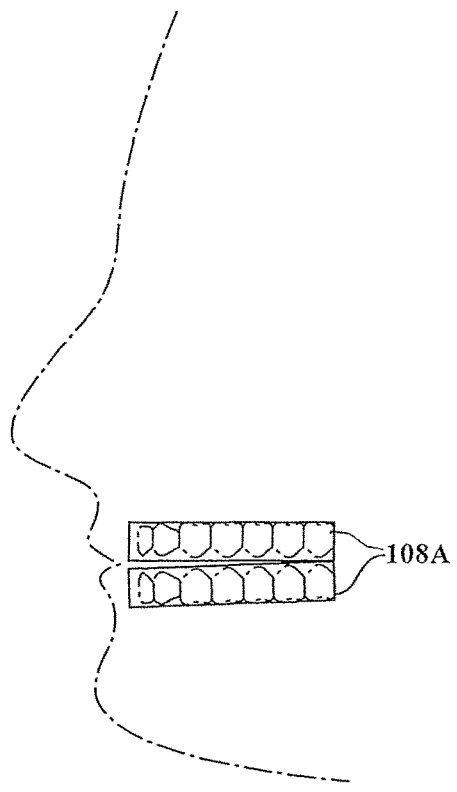
FIG. 8A is a drawing illustrating a side view of an embodiment of an inventive apparatus in place inside a user's mouth.
Figure 8B:
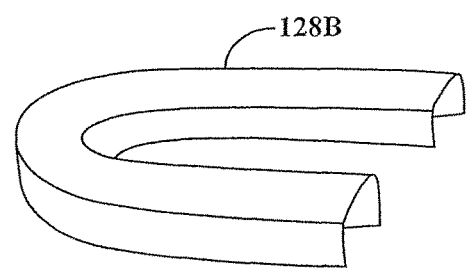
FIG. 8B is a drawing illustrating a perspective view of an inventive apparatus.

The support structure may have any of various forms determined according to the form of whitening composition used, choice of tooth to be treated, the number of dental treatments to be performed and the length of time over which a single dental treatment is performed. Support structures for dental treatment illustratively include a strip of sheet material and a shaped dental tray approximating the shape of a tooth, part or all of a dental arch or both dental arches. A typical dental tray has a U-shape in order to fit the average dental arch and channels are formed therein for insertion of the teeth during treatment. FIG. 8A illustrates an embodiment of the apparatus 108A in place in a user's mouth wherein the support structure has the form of a dental tray. FIG. 8B illustrates a U-shaped support structure 128B.

Figure 9A:
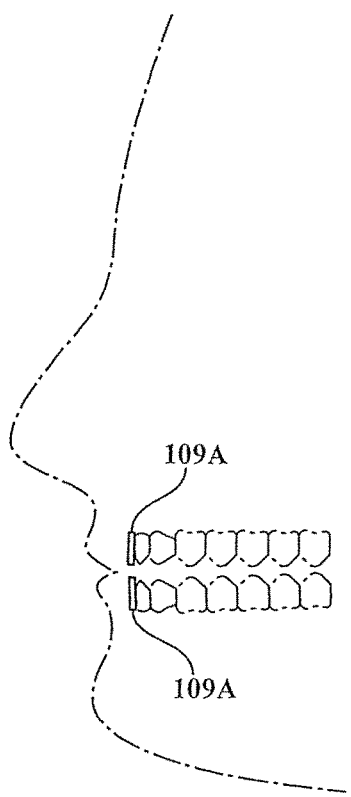
FIG. 9A is a drawing illustrating a side view of an embodiment of an inventive apparatus in place inside a user's mouth.

Particularly preferred is a support in the form of a tape or strip. FIG. 9A illustrates an embodiment of the apparatus 109A in place in a user's mouth wherein the support structure has the form of a sheet material. Further, support structures of the type useful in the present invention are those fabricated to conform to an individual's dentition, as is commonly performed in making dental tools such as bite splints, dental trays for medication delivery etc. The support may be formed to contain, cover or adhere to one tooth or multiple teeth at a time, and one or multiple surfaces of the teeth, such as front and back. This support allows selective treatment, such as treatment of front and back surfaces of front teeth only or treatment of all teeth, as desired. Supports in tape or strip form are exemplified in U.S. Pat. Nos. 5,891,453; 5,894,017; 5,989,569 and 6,045,811.

In a preferred embodiment, a support structure is provided as a moldable sheet material. The sheet material preferably has a shape which generally conforms to the shape of a human dental arch, that is a U-shape. The sheet material is molded in place in the user's mouth to conform to a user's dentition. An example is shown in FIG. 13 at 7000 and FIG. 14 at 9000. Referring to the support structure provided as a sheet material generally conforming to a human dental arch as a U-shaped sheet material, the U shape has two generally parallel and laterally disposed portions, exemplified as 7002 and 7004 in FIG. 13. Further, a support structure provided as a U-shaped sheet material has a connecting portion in contact with one end of each of the two lateral portions. In FIG. 13 the connecting portion is shown at 7006. A support structure provided as a U-shaped sheet material is dimensioned such that it is moldable to form a dental tray that fits virtually any person. Dimensions of the generally U-shaped sheet material provided are typically in the range of about 0.1-5 millimeters thick, preferably about 0.2-3 millimeters in thickness, also described as depth herein. A U-shaped support structure is typically configured to extend in length from the front teeth to about the distal edge of the premolars, i.e. the edge closer to the molars. Thus, in the embodiment shown in FIG. 13, the distance 7008 is generally about 2-8 centimeters in length, this distance is also termed the length of the U-shaped sheet material herein. The length is generally the distance from a midpoint on a front edge of the sheet material to a point at the midpoint between the lateral edges at the rear of the sheet material. Further, a U-shaped support structure is configured to extend across the mouth to contact teeth on both left and right sides of the user's mouth. Thus, the width of a U-shaped sheet material configured to achieve this requirement is typically about 4-10 centimeters in width and preferably 5-7 centimeters in width. The width dimension is shown in an exemplary embodiment in FIG. 13 as 7010. In a preferred embodiment, the width from a lateral edge of a first lateral portion to a lateral edge of a second lateral portion ranges from about 4-10 centimeters in width and preferably 5-7 centimeters in width. Further, the distance from a lateral edge of a first lateral portion to a medial edge of the first lateral portion ranges from about 1-4 centimeters. Preferably, the distance from a lateral edge of a second lateral portion to a medial edge of the second lateral portion also ranges from about 1-4 centimeters and is equal to the dimension of the distance from a lateral edge of a first lateral portion to a medial edge of the first lateral portion. Each lateral portion includes a rear edge, shown in FIG. 13 as 7012. The angle formed between a lateral edge of a lateral portion and a rear edge of the lateral portion is preferably a 90 degree angle. Similarly, the angle formed between a medial edge of a lateral portion and a rear edge of the medial portion is preferably a 90 degree angle. Such an embodiment is illustrated in FIG. 13 where the angle formed between a lateral edge of a lateral portion and a rear edge of the lateral portion is shown at 7014 and the angle formed between a medial edge of a lateral portion and a rear edge of the medial portion is shown at 7016. In other embodiments, the angle may be acute or obtuse as desired to treat specific teeth. Further, corners adjacent angles 7014 and 7016 may optionally be rounded. An exemplary embodiment has a width of 5.5 centimeters, a length of 3.8 centimeters and a thickness or depth of 0.2 centimeters.

A preferred moldable support structure is provided as a substantially planar sheet material. Such a support structure has a textured surface including multiple depressions or reservoirs for various whitening compositions including whitening agents and therapeutic agents as well as for disposition of a light source. In a preferred embodiment, a support structure may have one textured surface and one non-textured surface. In general the sheet material support structure is positioned such that the textured surface is facing the teeth in a user's mouth. The sheet material support structure is preferably dimensioned such that the textured surface is positionable in a human mouth such that the surface is in contact with an occlusal surface of 2-14, preferably 6-10 contiguous teeth on an upper or lower dental arch. The term occlusal surface is used herein to designate the surface conventionally understood to be occlusal tooth surface, such as those of the molars and premolars. The term occlusal surface is also used herein to include an incisal surface of the anterior teeth.

The moldable sheet material support structure in the shape of a dental arch, as exemplified in FIG. 13, is transformed into a dental tray by molding to fit a user's dentition. In a preferred embodiment, the moldable sheet material in the shape of a dental arch is provided in a substantially planar configuration and then molded into a three dimensional dental tray to custom fit the user at the time of use. For example, the moldable support is formed by direct application to the user's dentition and molding in place. Particularly preferred is a sheet material moldable at the time of use to form a custom fit dental tray. In addition, a preferred sheet material is moldable without application of heat. Thus, for example, a user molds the sheet material with pressure from the fingers or tongue to fit his or her dentition as desired, using no heat other than that from the user's hand or mouth.

Figure 13A:
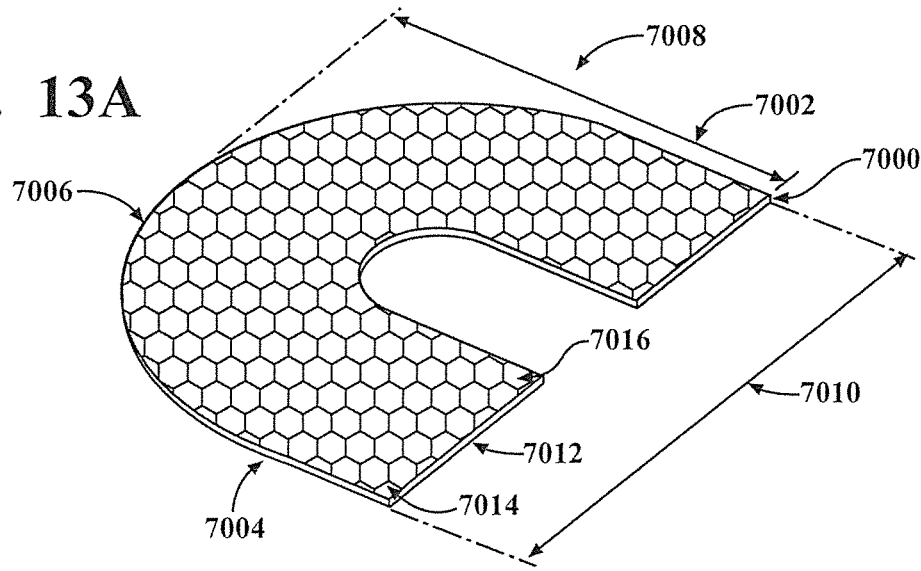
FIG. 13A is a drawing illustrating an embodiment of an inventive apparatus.
Figure 13B:
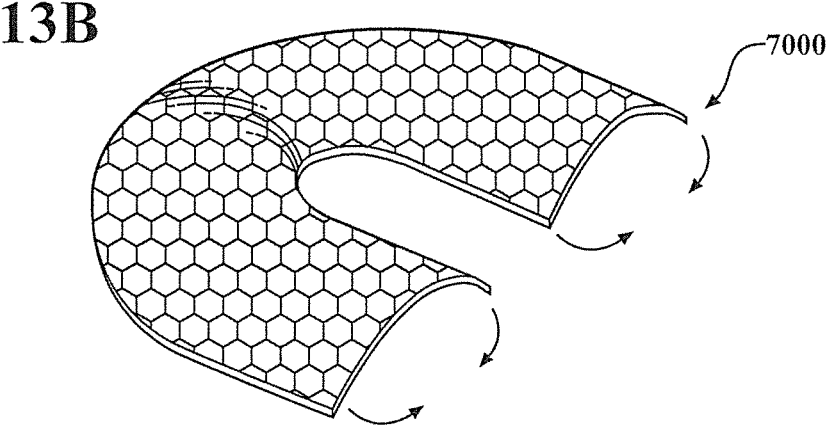
FIG. 13B is a drawing illustrating an embodiment of an inventive apparatus.
Figure 13C:
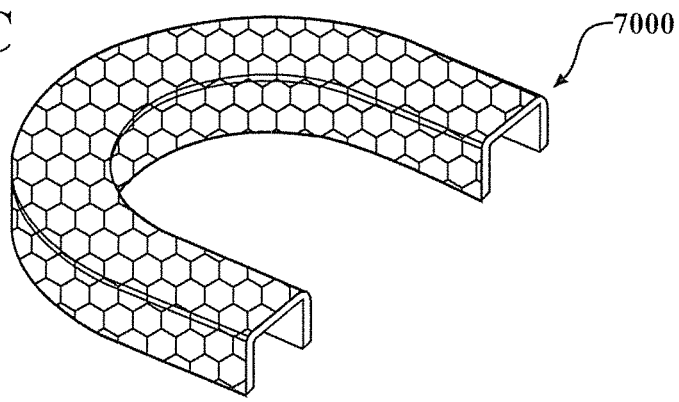
FIG. 13C is a drawing illustrating an embodiment of an inventive apparatus.

FIG. 13A shows a support structure 7000 in the form of a sheet material. The sheet material is transformed by molding, shown illustratively in FIG. 13B at 7000, into a dental tray, shown in an exemplary fashion at 7000 in FIG. 13C.

In a preferred embodiment, the U-shaped moldable support structure sheet material includes a light source in the form of a particulate phosphorescent material as shown in FIG. 14 at 9000.

In a preferred embodiment, a moldable support structure is provided as a sheet material which is transformed by molding into a dental tray. In particular, the support structure sheet material is moldable without heating. Thus, a support structure sheet material is moldable at a temperature ranging from about 10°-40° C. In a preferred embodiment, the material is moldable at room temperature without heat added, other than that incidentally transferred from the hand of the person molding the tray or from the mouth of the user.

A preferred moldable dental tray composition includes a wax, or is composed primarily of a wax, such as paraffin or beeswax. A support in the form of a sheet material including a wax is moldable such that a dental tray is formed by application of the sheet material to the dentition. Advantageously, a moldable material allows formation of a custom fit dental tray in minutes or less, in some cases almost instantly. Further, the custom fit dental tray may be molded to fit the user's teeth at the time of use.

In one embodiment, the support structure includes a reflective material disposed in or on the support structure so as to direct light toward the tooth to be whitened. Exemplary reflective materials include a white or silver coating, a metallic surface, metallic particles or metallic insert, so as to direct light toward the tooth to be whitened.

A support structure may have one or more textured surfaces. A textured surface promotes the adherence of the structure to the dentition and promotes contact between the whitening composition and the tooth to be treated. A textured may include bumps or protrusions in a regular or irregular pattern. A textured surface is generated by various methods, illustratively including embossing.

Figure 9B:
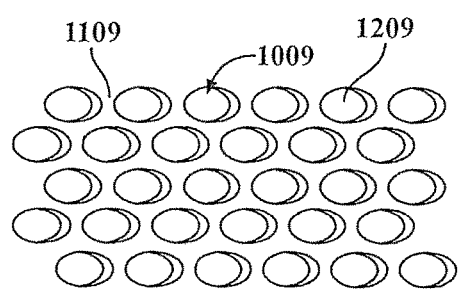
FIG. 9B is a drawing illustrating a textured surface of a support structure.
Figure 9C:
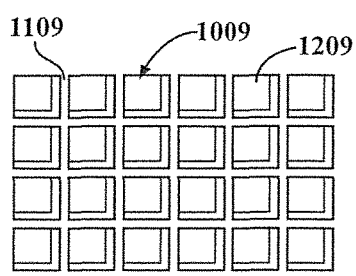
FIG. 9C is a drawing illustrating a textured surface of a support structure.
Figure 9D:
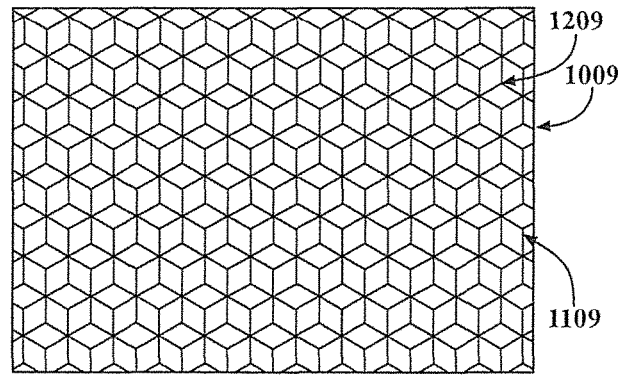
FIG. 9D is a drawing illustrating a textured surface of a support structure.
Figure 9E:
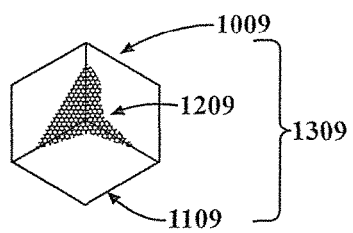
FIG. 9E is a drawing illustrating an individual cell included in a textured surface of a support structure.

Optionally, a support structure includes a reservoir for holding whitening composition to be delivered to a tooth to be treated. For example, a reservoir may be a textured surface that includes a pattern of shaped individual cells in the support structure surface. Each cell includes a wall defining a shape of the cell, and a central depression. The individual cell may have any shape including a geometric shape such as a circle, oval, a polygon, illustratively including a square, rectangle, triangle hexagon or other regular or irregular shape. Cells included in a support structure may all have the same shape and same size or cells may differ depending on such factors as, for example, the viscosity of the composition used and the tooth or teeth to be treated. Examples are shown in FIGS. 9B, 9C and 9D, illustrating shaped cells 1009, each having a wall 1109 and a central depression 1209. Typically, an individual cell has a diameter (or a largest dimension) 1309 that ranges in length from about 0.1 to 15 millimeters. A central depression 1209 ranges in depth from about 0.1 to 4 millimeters. In a preferred embodiment, the cell is hexagon shaped, forming a honeycomb pattern on a surface of the support structure. An example of a preferred hexagonal pattern is shown in FIG. 9D. The hexagonal cells forming the honeycomb pattern may all have the same size or may differ in size. In a preferred embodiment, an individual hexagonal cell, as shown in FIG. 9E, has 6 sides of equal length, a diameter 1309 ranging from about 5 to 6 millimeters and a central depression 1209 having a maximal depth of about 0.1 to 4, preferably 2.0, millimeters.

Figure 9F:
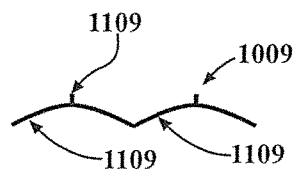
FIG. 9F is a drawing illustrating a cross-section of a textured surface of a support structure.
Figure 9G:
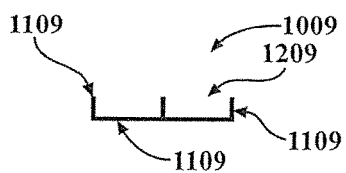
FIG. 9G is a drawing illustrating a cross-section of a textured surface of a support structure.

A wall 1109 of an individual cell 1009 divides one cell from another and defines the central depression 1209 A wall 1109 may slope towards the central depression 1209, as shown in cross-section in FIG. 9F, or a wall 1109 may have straight sides as shown in cross-section in FIG. 9G.

Composition of a Support Structure

The support structure may be made of any of the typical biocompatible materials used in forming dental apparatus. Resins, plastics, waxes and the like may be used to form sheet material or a suitable shape by methods such as injection molding or casting. Thermoset and photocurable materials may be used, particularly for support structures formed to the individual's dentition. Illustrative examples of synthetic polymers used include polyurethanes, polyvinyl chlorides, acrylates, including ethyl vinyl acrylate, polycarbonate, polyphenylene oxide, polyimide, polyethylene, polypropylene, polystyrene, polyvinyl chlorides, polyamides and polyesters, acetates including ethyl vinyl acetate, combinations thereof and art recognized equivalents. Natural materials may also be used, including natural waxes, plant fiber materials such as cellulose, and the like. Preferred materials include beeswax and paraffin. Further, mixtures of such materials may be used.

For example, a preferred support composition includes paraffin or beeswax. A support in the form of a paraffin or beeswax sheet is moldable such that a dental tray is formed by application of the sheet material to the dentition. Advantageously, a moldable material allows formation of a custom fit dental tray in minutes or less, in some cases almost instantly.

The finished support may have a relatively supple consistency such as a gel, foam or wax such that teeth are not damaged by contact therewith. In a preferred embodiment a support structure is has a gel-like consistency. A gel-like support structure may be formed from materials including exemplary materials such as gelatin, silicone, gelled mineral oils, and the like. Further, materials such as the Versagel C or M series (Penrenco) or other di-block, tri-block, multi-block and radial block copolymers such as the Kraton G series polymers (Shell Chemical) are suitable for use in the invention. Other exemplary materials that may be used include gelled Permethyl 99A-750, 99A-753-59, and 99A-753-58 triblock and starburst polymer mixture, OS129880, OS 129881 and OS 129883 from Lubrizol (a styrene/methacrylate copolymer), Viscogel by Laviosa Chimica Mineraria, silicone products such as Medical Adhesive A, 7-9800, RTB 700,732,736 by Dow Corning and dimethicone copolyols such as Dow Corning 3225C and lauryl methicones such as Dow Corning Q2-5200 all by Dow Corning Company.

Advantageously, the support may include an adhesive for promoting adherence to the dental surface, for instance a tooth or teeth.

Light Sources Included in an Apparatus

Light sources and wavelengths of light providing energy that promotes activation of dental whitening compositions are described herein.

A light source may be a luminescent source, such as fluorescent, phosphorescent or chemiluminescent. Other exemplary light sources include light emitting diodes and laser diodes. These light sources are powered in a manner such that the light is emitted in the mouth without external connections to a power source. For example, light emitting diodes and laser diodes operable in the present invention may be powered by an energy storage device such, as a battery or capacitor, incorporated into the apparatus. A chemiluminescent source is powered by mixing appropriate chemical reactants so that a light producing reaction occurs during treatment. A fluorescent or phosphorescent source included in the apparatus is powered by exposure to exciting light so that fluorescent or phosphorescent light is emitted during dental treatment. For example, a phosphorescent source may be held under exciting light for a period of time before placement in the patient's mouth for dental treatment. Alternatively, a phosphorescent source may be placed in the patient's mouth and subsequently exposed to exciting light while the patient's mouth is open. The phosphorescent afterglow then continues to activate the whitening compound after the patient closes the mouth.

Combinations of light sources are specifically contemplated as within the scope of the invention. For example, a fluorescent source may be used in conjunction with a second light source, such as a phosphorescent light such that the fluorescent source is excited by the emitted phosphorescent light. Similarly, combinations of diode sources and phosphorescent or fluorescent sources may be used.

In addition to light sources described above, a light source included in a dental apparatus may be a chemiluminescent light source provided in microencapsulated form. Reaction components are separately incorporated into microcapsules, such as alginate beads. Components are mixed by placing reaction component containing beads in proximity and releasing the components from the beads by application of pressure, dissolution of the capsule barrier, warming or similar release methods, such that the components react and produce light. For example, in accordance with the invention, an oxalate compound and a fluorophore may be stored microencapsulated together, and hydrogen peroxide microencapsulated separately. These two forms of microcapsules are applied to a support, such as a honeycomb textured moldable sheet, or directly to a dental surface, such as a tooth or teeth. A chemiluminescent reaction may then be initiated by releasing the reaction components from the microcapsules. The reaction components are thus mixed, initiating the chemiluminescent reaction and producing light. One of skill in the art will recognize that other combinations of chemiluminescent reactants are operable in this embodiment. It is appreciated that a hydrogen peroxide solution used in this context as a component of a chemiluminescent reaction, is also a whitening composition component.

In another embodiment, one component of a chemiluminescence reaction may be microencapsulated and other reactants provided in another form. The microspheres are permeabilized so that the reactants contained therein are released into contact with the other reactants, allowing the chemiluminescent reaction to occur. For example, microspheres containing an oxalate compound and a fluorophore may be applied to a support, such as a honeycomb textured moldable sheet, or directly to a dental surface, such as a tooth or teeth. A hydrogen peroxide containing liquid, gel, emulsion, putty, paste or the like is also applied to the support or a tooth to be whitened. The microencapsulated components are released, by application of pressure, enzymatic or solvent mediated dissolution of the capsule barrier, warming or similar release methods. Released microencapsulated components then react with the other reaction components so that a chemiluminescent reaction occurs. One of skill in the art will recognize that other combinations of chemiluminescent reactants are operable in this embodiment. It is appreciated that a hydrogen peroxide solution used in this context as a component of a chemiluminescent reaction, is also a whitening composition component.

In a further embodiment, as described above, one component of a chemiluminescence reaction may be microencapsulated and other reactants provided in another form, such as a solution. In this case, the microspheres are made permeable to molecules of selected size, in order to allow other reactants to diffuse into the microspheres but preventing release of microencapsulated components. The interaction of the reaction components initiates a light producing reaction inside the microspheres. For example, microspheres containing an oxalate compound and a fluorophore may be applied to a support, such as a honeycomb textured moldable sheet, or directly to a tooth to be whitened followed with a hydrogen peroxide containing liquid, gel, emulsion, putty or paste. In this case, the microspheres are made permeable to molecules of selected size, in order to allow hydrogen peroxide to diffuse into the microspheres but not allowing release of the oxalate compound and fluorophore. One of skill in the art will recognize that other combinations of chemiluminescent reactants are operable in this embodiment. It is appreciated that a hydrogen peroxide solution used in this context as a component of a chemiluminescent reaction, is also a whitening composition component.

Disposition of a Light Source in Relation to a Support Structure of an Apparatus A light source may be disposed on and/or in the support structure so that light emitted from the light source impinges on the whitening composition.

Figure 10A:
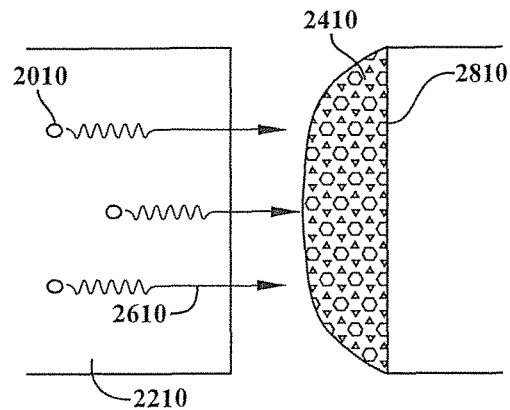
FIG. 10A is a drawing illustrating an embodiment of an inventive apparatus.

In another embodiment, a light source is made integral to the support by being included in a material forming the support structure. In an embodiment shown in FIG. 10A, a luminescent material light source 2010 is integral to the support structure 2210. Also shown is a dental whitening composition 2410 which is contacted by light 2610 emitted by the light source 2010. The dental whitening composition is shown in contact with a dental surface 2810. Methods and compositions for forming luminescent articles by including a luminescent material in a resin, plastic, wax, sheet material or other support structure forming material include, for example, those described in U.S. Pat. Nos. 3,796,668; 4,211,813; 4,629,583; 4,707,297; 4,911,830; 5,464,651; 5,618,467; 5,783,108; 5,914,076 and 6,375,864.

Figure 10B:
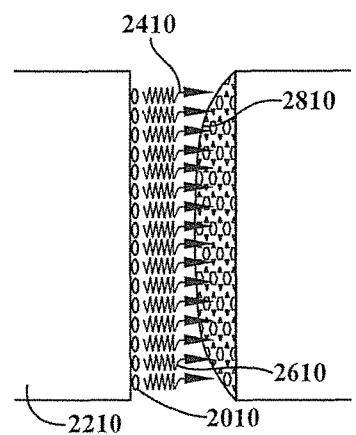
FIG. 10B is a drawing illustrating an embodiment of an inventive apparatus.
Figure 10C:
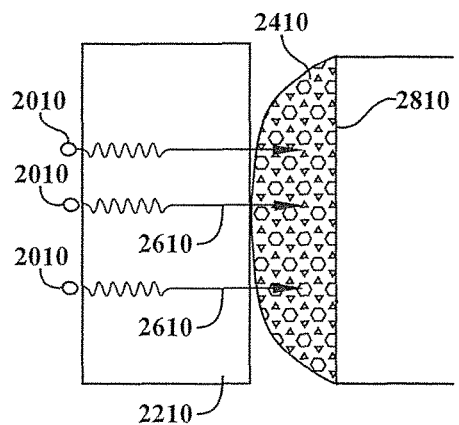
FIG. 10C is a drawing illustrating an embodiment of an inventive apparatus.

Alternatively, a diode or luminescent material may be disposed on an external surface of a support. In an embodiment shown in FIG. 10B, a light source 2010 is present on an external surface of a support structure 2210. Also shown is a dental whitening composition 2410 which is contacted by light 2610 emitted by the light source 2010. The dental whitening composition is shown in contact with a dental surface 2810. FIG. 10C illustrates an arrangement wherein the light source 2010 is on a surface of the support structure 2210 distal to the dental surface 2810 which is in contact with the whitening composition 2410. A light source disposed on a support structure may have various forms illustratively including a diode and a luminescent material in the form of a gel, gum, emulsion, putty, liquid paint, varnish, curable resin, wax, tape, glow tube, glow stick or paste which can be applied to a support.

A diode and its power source may be applied to a support structure surface by conventional methods illustratively including adhesive fixation. Similarly, a luminescent light source in may be affixed to a support using an adhesive. Suitable adhesives preferably include food grade adhesives such as Spectrum 0172, available from the Velcro Group Corporation, and other materials such as those disclosed in U.S. Pat. Nos. 3,527,646; 4,504,502; 4,910,031; 4,913,919; 4,981,707; 5,275,830; 5,275,831 and 5,298,268.

Optionally, a protective material covers the light source and/or whitening composition. For example, a layer of a sheet material, such as polypropylene, polyvinylidene chloride, polyethylene and the like, is placed over the light source and/or whitening composition. The protective material may be placed over a whitening composition for instance where the composition is applied to the support in advance of use, such as during manufacture, so as to protect the composition from dehydration, exposure to light, air and the like. The protective material may then be removed just prior to use.

Similarly, an optional protective material may be disposed so as to cover a light source in order to aid in securing in the light source to the support and to protect the light source from the environment. In one embodiment, a light source includes a phosphorescent powder affixed to a surface of a moldable sheet material support structure using an adhesive. Optionally, a protective sheet material is affixed to the same surface of the support structure after application of the phosphorescent powder. The protective sheet material aids in keeping the phosphorescent powder in place on the support and protects the powder from exposure to the environment. The protective sheet material may be translucent to allow excitation of the light source and/or emission of the phosphorescent light.

A protective sheet may also be present on a support structure for other reasons, for example, to protect the support structure, light source, whitening composition or from contamination by dirt, microorganisms and the like. A protective sheet may also be configured to prevent dehydration of a support structure, and associated components.

In some embodiments, a protective sheet remains in contact with a support structure during use. For example, a protective sheet optionally remains in place to separate a light source from direct contact with the user's teeth or mouth.

A light source may be disposed on, integral to, or in a support structure in multiple forms in an inventive apparatus. For instance, a light source may be incorporated in a material included in or forming the support structure. In addition, a light source may be applied to the support structure.

Advantageously, a light source may be disposed in relation to the support such that only teeth to be treated are exposed to the light. For example, a light source in the form of a gel may be placed in proximity to a subset of teeth. Similarly, a diode source may be positioned where desired on a support such that light is directed primarily a certain tooth or teeth to be treated. Further advantageously, a light source and whitening composition may be disposed on a support such that both the front and rear of the teeth may be whitened. Since teeth are translucent to some extent, the color of the rear surface of a tooth influences the perception of tooth color as viewed from the front. Thus, an inventive apparatus and method allow for increased whitening.

Further, a light source may be placed so that multiple areas of a tooth may be treated simultaneously. For example, a support incorporating a luminescent substance may be formed to fit the individual's dentition so that both the front and back of a tooth are exposed to a whitening compound and activating light. An inventive light-activated system allows for simultaneous light accelerated whitening of the front and back of a tooth, as well as lateral aspects of the tooth, with no protruding parts (i.e., with the mouth closed).

A luminescent material or diode may be partially or wholly surrounded by support structure material such that light is transmitted through the support structure to the dental whitening composition. In one embodiment of this arrangement (not shown), a chemiluminescent light source may be located in an interior chamber of the support structure such as a fluid-tight internal cavity for a chemical reactant. The internal cavity is sub-divided into at least two compartments, each containing a chemical reactant. The compartments are separated by an internal divider which can be broken so as to mix the chemical reactants such that a chemiluminescent reaction occurs, producing light.

Figure 10D:
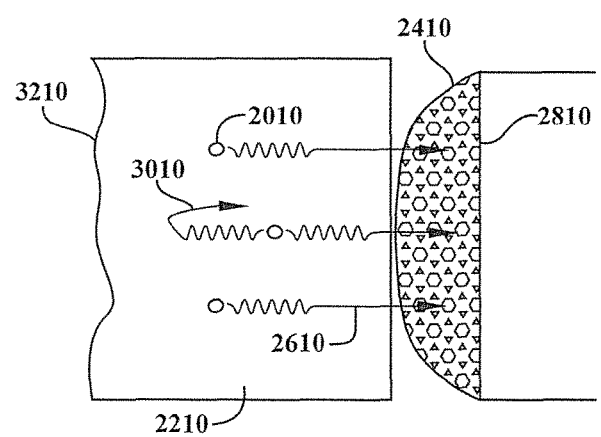
FIG. 10D is a drawing illustrating an embodiment of an inventive apparatus.

In an embodiment shown in FIG. 10D, a light source 2010 is integral to support structure 2210. The light source 2010 emits light 2610 which travels toward the dental whitening composition 2410 as well as light 3010 traveling in other directions. A reflective material 3210 included in the apparatus directs light 3010 toward the whitening composition.

Figure 11:
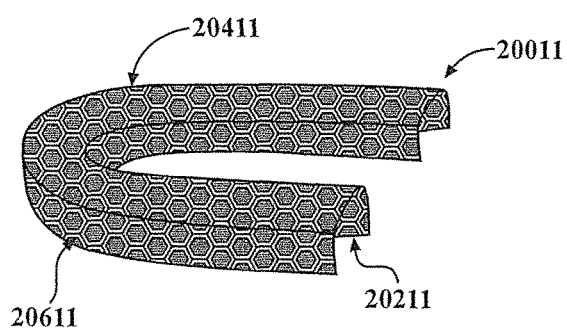
FIG. 11 is a drawing illustrating an embodiment of an inventive apparatus.

In one embodiment of an inventive apparatus, shown in FIG. 11, a support structure having a generally described U-shape is shown at 20011. A textured surface 20211 is shown including hexagonal cells 20411. The cells 20411 act as reservoirs for delivery of whitening compositions and here are shown containing beads 20611 which enclose a whitening composition, such as hydrogen peroxide in a concentration ranging from 3-35%. A phosphorescent light source (not shown) is integral to the support shown, such that when an exciting light is directed at the support for a period of time, the support glows for a period after the exciting light is removed. The apparatus shown may be provided in the generally described U-shape shown and then molded to conform to the user's teeth at the time of use. Preferably, the support structure is provided as a sheet material including cells as described, then molded to provide a custom fit apparatus at the time of use.

Size of Dental Apparatus

The dental apparatus is sized to fit entirely within the mouth of a patient while the patient undergoing dental whitening. Thus, the support structure and light source are in place and operable while the patient's mouth is closed. Further, because it is not necessary to attach the apparatus to an external power source during treatment, the patient can move freely and go about normal activities without any wires, fibers, batteries or other connections, such as to a power or light source, protruding or extending outside the mouth in the course of treatment. Typical size of an apparatus is ranges from about 0.5 cm$^3$ to about 450 cm$^3$ and is less than the volume of an average adult human oral cavity which ranges from about 100 to 500 cm$^3$.

Apparatus Including a Whitening Composition

In another embodiment of the invention, an apparatus is provided which includes a whitening composition as described herein. A whitening composition may be applied to, or incorporated in, a support structure so that when the apparatus is placed in the user's mouth, the whitening composition contacts a dental surface to be whitened.

In one embodiment, the whitening composition is incorporated in the support structure from which it is extruded or leeches onto the dental surface while the patient wears the apparatus. For example, carbamide peroxide may be included in a support structure composed of an anhydrous gel such that when the support is placed in the mouth of a user, the carbamide peroxide leeches from the gel into the aqueous environment of the dental surface. In another example, a tape or strip support structure may be coated with a layer of whitening composition. Whitening composition may be applied to the support structure at anytime, such as during manufacture, or just prior to use. In another example, a tape or strip may contain microencapsulated gel-like beads containing hydrogen peroxide. This strip may be cut or separated at the desired length and applied to the tooth surface.

In a preferred embodiment, a whitening composition in the form of hydrogen peroxide microencapsulated in gel-like beads, such as alginate beads, is applied to a moldable support structure having a honeycomb textured surface. The moldable support structure is composed of a pliant material such as wax or other material which readily conforms to the shape of the teeth. The support material may be molded by hand at room temperature. This combination has excellent delivery properties due in part to the close adaptation of the honeycomb shapes on the support surface to the smoother surface of the teeth which may be aided by Van der Walls forces between these surfaces. In use, the encapsulated whitening agent is released by application of pressure, heat or light.

As noted above, a whitening composition may contain a therapeutic agent such as an agent to treat dental or systemic diseases or conditions, including a toothpaste, mouthwash, anti-plaque agents, anesthetics, desensitizing agents, analgesics, antibiotics, antifungals, antimicrobials, antivirals, anti-inflammatory agents, steroids, remineralizing agents, and anticariogenic agents. Optionally, any of these agents may be included in an inventive apparatus and/or provided as part of an inventive method.

Separator

In an embodiment of the present invention, a separator is provided. A separator is used to separate a tooth or teeth being treated with a whitening composition from other oral structures, such as lips, cheek and tongue. Further, a separator may be used to help keep an optimal amount of the whitening composition in contact with the tooth or teeth being whitened. For example, a separator is illustratively a cotton roll, braided or unbraided, which may be placed between the cheek and gum to extend the distance between the cheek and the tooth or teeth being treated. In another embodiment, a separator is an apparatus as described herein.

Predetermined Amount of a Whitening Composition

A predetermined amount of a whitening composition is dispensed by the delivery device in response to user activation of a button, lever, ratchet or the like. The predetermined amount is determined according to the application and the content of the delivery device. Generally, a delivery device according to the invention reproducibly dispenses an amount in the range of 1-500 microliters in response to each user activation event. The amount desired to be dispensed by a dispenser in response to each user activation event will vary depending on the formulation of the whitening composition contained in the delivery device. For example, a more viscous formulation will adhere to an applicator tip longer than a less viscous formulation and thus a larger amount of the viscous formulation may be transferred to the tooth without dripping. Further, a more concentrated whitening composition, such as 20 percent peroxide, may be dispensed in smaller amounts than a less concentrated agent, such as 6 percent peroxide, in order to aid in preventing application of concentrated whitening composition to non-tooth tissue. The particular predetermined amount preferred for a particular formulation is easily determined by one of skill in the art.

Applicator Tip

An applicator tip included on a delivery device preferably includes a brush for application of whitening composition to a tooth. The brush has a length and width, each of which is dimensioned according to the particular application. Total brush length is determined by the longest brush bristle length, discussed below. Brush width typically ranges between 0.1-0.5 inches. Brush bristles may be uniform in length or have varying lengths. In one embodiment, bristles are graduated in length, providing an increased surface for whitening composition application. Bristle length may be varied in some embodiments by including a retractable applicator tip. The longest bristle in a brush applicator tip ranges between 0.1-0.5 inches.

In an alternative embodiment, an applicator tip may include a sponge, swab or roller for whitening composition application.

The applicator tip may be integral to the delivery device, such as a device formed by injection molding. Alternatively, the applicator tip is attachable to the body portion of the device, for instance by snap-on interlocking engagement or threaded engagement. One attachable tip may be interchanged with another as desired, for example, a tip may be disposed of after use and replaced by an unused tip for increased hygiene.

Application

The predetermined amount of whitening composition disposed on the applicator tip is applied to a tooth to be whitened. To this end the applicator tip is brought into contact with a tooth such that whitening composition is deposited on the tooth. In an optional further step of a method, the applicator tip may also be used to spread the deposited whitening composition over the tooth.

Incubation of Whitening Composition on Tooth

The whitening composition is allowed to remain in contact with the tooth for a period of time sufficient to whiten a tooth. Typically, a user allows the agent to remain in contact with the tooth by refraining from brushing the tooth, eating, drinking or otherwise wiping the whitening material from the tooth. The period of time sufficient to whiten a tooth will depend on variables such as the whitening composition used, the extent and type of staining of the user's tooth and the amount of whitening composition used. Generally a sufficient period of time ranges between 1 minute and 24 hours. The period of time sufficient to whiten a tooth using a particular whitening composition is determined according to standard tests used in the dental profession. For example, a standard test to determine a time sufficient to whiten a tooth using a particular whitening composition includes application of the whitening composition to a set of excised or artificial teeth. The excised or artificial teeth are evaluated for intensity and color of staining followed by incubation of various amounts of the whitening composition for various periods of time. The test teeth are re-evaluated for intensity and color of staining to determine whether and to what extent whitening has occurred.

Evaluation of initial staining and staining following treatment may be performed by eye by an experienced clinician. Alternatively, evaluation may be performed by objective analysis such as by digital imaging in combination with computer-assisted image analysis. For instance, an initial image of a tooth to be treated is acquired under reproducible lighting conditions and the image transferred to a computer database. The image is preferably acquired with a grayscale standard within the image frame. The grayscale value of various areas of the tooth surface are recorded along with xy coordinates of these areas. Following treatment the tooth is re-imaged as described and grayscale values of the image compared with initial values in order to obtain a measure of whitening. Further methods of determining a period of time sufficient to whiten a tooth illustratively include those described in the following references:

1.) Nathoo, S A, The chemistry and mechanisms of extrinsic and intrinsic discoloration., J. Am. Dent. Assoc. 128 Suppl:6 S-10S, 1997
2.) Amaechi, B T, Higham, S M, Development of a quantitative method to monitor the effect of a tooth whitening composition., J. Clin. Dent. 13(3):100-103, 2002
3.) Jones A H et al., Colorimetric assessment of laser and home bleaching techniques., J. Esthet. Dent. 11(2):87-94.
4.) Bentley, C, Quantitation of vital bleaching by computer analysis of photographic images., J. Am. Dental Assoc. 130(6):809-816, 1999.

Process of Whitening A Tooth

A process of whitening a tooth according to the present invention includes several steps. In a step according to the inventive process, a delivery device for mechanical dispensing of a predetermined amount of a whitening composition to an applicator tip is provided. Another step is that of dispensing the amount of whitening composition to the applicator tip. In a further step, the user applies the amount of whitening composition disposed on the applicator tip to the tooth to be whitened. Also, in a further step, the user allows the whitening composition to remain in contact with the tooth for a period of time sufficient to whiten a tooth.

In a preferred embodiment, an inventive process further includes a step of exposing a whitening composition to light. Optionally, the whitening composition is exposed to light while the composition is in contact with the dispensing device. For example, the composition is exposed to light while in a reservoir and/or flow tube of a dispensing device.

Further, the composition is optionally exposed to light while disposed on the applicator tip.

In a further option, the whitening composition is exposed to light after applying the amount of whitening composition to the tooth to be whitened. For example, an optional step of an inventive method is exposing the whitening composition on a tooth to light emitted from a light source which is disposed on the mechanical dispensing device. Thus, configurations of a device including a light source include disposition of a light source such that it can be directed into a user's mouth.

In another embodiment, an inventive process includes the step of providing a dental apparatus wherein the dental apparatus includes a support structure adapted to be placed entirely within a user's mouth and has a light source disposed on or in the support structure such that light emitted from the source impinges on the dental whitening composition on the tooth to be whitened. The apparatus has a volume between 0.5-450 cm$^3$ and thus fits entirely within a user's mouth during use, with no protruding parts.

In a preferred embodiment, the dental apparatus is moldable to conform to the user's dentition. In particular, as described above, a preferred apparatus is moldable to fit the user's dentition at the time of use. Thus, a preferred apparatus is a moldable sheet material including a wax, or composed primarily of a wax, and, including a light source, which is applied to a user's dentition following application of a whitening composition to the dentition or a portion thereof, and molded to achieve a custom fit. Particularly preferred is an apparatus provided as a wax or wax containing sheet material which has a textured surface as described herein, especially a honeycomb-like hexagonal textured surface. Further preferred is an apparatus provided as a wax or wax containing sheet material which has a textured surface and wherein the light source is a phosphorescent material included in the sheet material. Also preferred is an embodiment in which an apparatus provided as a wax or wax containing sheet material which has a textured surface and wherein the light source is a phosphorescent material disposed on the sheet material in a particulate form. In such an embodiment a protective sheet material, preferably translucent to light exciting and emitted by the phosphorescent material, is optionally included to cover a surface on which the phosphorescent material is disposed. Optionally, the dental apparatus includes a dental whitening composition in contact with the support structure. A protective sheet is optionally included to cover a surface on which a whitening composition is disposed. A protective sheet is optionally removable as desired.

Chewing Gum or Confectionary Whitening Composition Delivery Device

A gum or confectionary composition is an inventive delivery system for a tooth whitening composition provided by the present invention, providing a pleasant tooth whitening experience for the user. Chewing gums and candies provide an excellent delivery system for a whitening composition, allowing sustained release of the whitening composition and distribution of the composition to teeth, even those in the rear of the mouth. Manufacture of chewing gums and confections is exemplified in references such as E. B. Jackson, Ed. "Sugar Confectionery Manufacture", 2nd edition, Blackie Academic & Professional Press, Glasgow UK, (1995).

An inventive chewing gum is formulated to include a gum base and a whitening composition. For example, the chewing gum includes a gum base which includes chewing gum ingredients illustratively including a natural or synthetic elastomer, a solvent, an emulsifying agent, a filler, a flavoring agent, a coloring agent and a sweetening agent. The whitening composition may be included in the gum base or in a cavity defined by a wall formed by the gum base as described below.

Exemplary elastomers include natural elastomers such as chicle, chilte, guayule, gutta percha, jelutong, tuno, and crown gum; and synthetic elastomers such as butadiene-styrene copolymers, isobutylene-isoprene copolymers, polyisobutylene, paraffin, petroleum wax, polyethylene, polyvinyl acetate, and mixtures thereof. Typically, an elastomer is present in a range of about 10% to 50% by weight, preferably from about 15% to about 30% by weight, of the chewing gum composition.

An elastomer solvent included in an inventive chewing gum composition illustratively includes a terpene resin, including polyterpene, and methyl, glycerol or pentaerythritol esters of rosins or modified rosins, including hydrogenated, dimerized or polymerized rosins or mixtures thereof. An elastomer solvent is typically present in an amount ranging from about 5% to 85% and preferably about 10% to about 50% by weight of the chewing gum composition.

An emulsifier present in an inventive chewing gum composition illustratively includes glycerine, glycerol monostearate, glycerol triacetate, lanolin, lecithin, stearic acid, triacetin, waxes such as natural waxes, petroleum waxes and microcrystalline waxes and fats and oils including animal fats such as lard and tallow, vegetable oils such as soybean and cottonseed oil, hydrogenated and partially hydrogenated vegetable oil and cocoa butter, and the like which are incorporated into the chewing gum composition as desired to obtain a particular texture. An emulsifier is optionally included in amounts ranging from 1-30% by weight, preferably 2% to 25% by weight and more preferably from about 3% to about 10% by weight of the chewing gum composition.

A coloring agent included in a chewing gum composition according to the invention illustratively includes coloring agents certifiable by the FDA and natural coloring agents such as annatto extract, beta-carotene, beet powder, canthaxanthin, caramel color, carrot oil, cochineal extract (cannine); cottonseed flour, fruit juice, grape extract, paprika, paprika oleoresin, riboflavin, saffron, turmeric and turmeric oleoresin. A preferred coloring agent is titanium dioxide. A coloring agent is optionally present in amounts ranging from 0.2%-5% by weight of the total gum composition.

A filler included in a chewing gum composition includes such as aluminum hydroxide, alumina, aluminum silicates, calcium carbonate, cellulose, dicalcium phosphate, magnesium carbonate, talc, and combinations thereof in amounts ranging from 5 to 25% by weight of the chewing gum composition.

A sweetener is optionally included in an inventive chewing gum composition, including a sugar such as sucrose, dextrose, maltose, fructose and the like; sugar alcohols such as sorbitol, mannitol, xylitol, malitol, isomalt, erythritol, hydrogenated starch hydrolysates; aspartame, acesulfame salts, aliatame saccharin and the like and combinations thereof. A sweetener is optionally present in amounts up to 90% by weight of the final composition. An inventive chewing gum composition optionally includes flavoring agents conventional in the art in amounts up to about 10%.

A number of U.S. Patents describe liquid or gel-filled gums, their composition and manufacture, including U.S. Pat. Nos. 6,652,839; 6,284,291; 5,922,347; 5,916,606; 5,912,030; 5,900,230; 5,885,630; 5,866,179; 5,858,423; 5,846,557; 5,834,002; 5,827,526; 5,824,291; 5,736,175;

4,156,740; 5,498,429; 4,466,983; 4,157,402; 5,569,477; 5,125,819; 5,248,508; 4,975,288; 4,792,453; 4,980,178; 4,683,138; 5,087,460; 4,292,329; 4,642,235; 4,316,915; 4,513,012; 4,250,196; 5,431,929; and 4,647,450. These patents are incorporated by reference herein in their entirety.

A chewing gum according to the invention optionally includes an external coating as is conventional in the art. For example, a chewing gum includes an a thin candy shell on the exterior of the gum.

An inventive confectionary delivery device is a candy including a confectionary base and a whitening composition. The whitening composition may be included in the confectionary base or separately in an internal cavity. A confectionary delivery device includes a confectionary base which contains confectionary ingredients, illustratively including a sweetener, a solvent, an emulsifying agent, a filler, a flavoring agent, and a coloring agent.

A chewing gum or confectionary embodiment comprising a gum or confectionary base configured to form a wall enclosing a cavity and a whitening composition disposed in the cavity is particularly preferred. FIG. 12A depicts a piece of tooth whitening gum or confectionery 6000 according to one embodiment of the invention. FIG. 12B shows a piece of gum or confectionary such as shown in FIG. 12A, cut along lines 12B-12B and illustrates a gum or confectionary base configured to form a wall 6100, enclosing a cavity 6200 with a whitening composition therein. Also shown is an external coating 6300 disposed on the exterior surface of the wall 6100 which is optional.

The whitening composition disposed in the cavity is formulated as a liquid, gel, microencapsulated liquid and microencapsulated gel. The whitening composition includes a whitening agent, preferably an oxidizing agent, and further preferably a peroxide, such as hydrogen peroxide, carbamide peroxide, and alkaline metal peroxides as described herein. The whitening composition optionally further includes an ingredient selected from the group consisting of: a solvent, an emulsifier, a buffering agent, a flavoring agent, a sweetener, a coloring agent a thickener, and a preservative. The whitening composition is present in an amount ranging from 1-50% of the total chewing gum composition by weight. Optionally the whitening composition is present in an amount ranging from 2% to 25% by weight of the total gum composition and further optionally from about 3% to about 10% by weight of the total chewing gum composition. In general, the ratio of gum base to whitening composition ranges from 10:0.1-0.1:1.0. A preferred ratio is 10:0.5-1:1. The volume of whitening composition generally ranges from about 50 microliters to about 1 milliliter.

Light Activation of a Whitening Composition in a Gum or Confectionary Delivery Device An external light source, such as an LED, may be used to activate a whitening composition in an inventive gum or candy delivery device. For example, light is directed towards the gum or candy for a time sufficient to activate the whitening composition prior to chewing the gum or candy. Alternatively, light is directed towards the teeth following chewing of the gum or candy such that the whitening composition is activated in place on the teeth to be whitened.

Optionally, a light source is included in the gum or candy delivery device. Such a light source may be itself activated by an external source, for instance, a phosphorescent or fluorescent light source activated by a source of appropriate wavelength. Another light source included in an inventive candy or gum is a microencapsulated chemiluminescent material which becomes activated so as to produce light upon chewing.

A process for whitening a tooth using an inventive gum or candy whitening composition delivery device is provided by the present invention. An inventive process includes the step of providing a gum or candy composition including a whitening composition to a user. A further step includes contacting the teeth with the whitening composition. In this step the user's teeth contact the whitening composition when the user chews or dissolves the gum or candy in the mouth, releasing the whitening composition. In another step, the whitening composition is incubated on a tooth to be whitened for a period of time sufficient to whiten the tooth.

Optionally, the process includes the step of repeating the steps of contacting the user's teeth and incubating the tooth with the whitening composition. For example, a gum or candy delivery device may be provided in a package containing a number of pieces of gum or candy to ensure a supply sufficient for a particular period of treatment, that is a one-day supply, one week supply, two week supply and the like. The number of pieces depends on the strength of the whitening composition and the amount of treatment necessary. Typically such a package may contain 2-100 pieces, preferably, 3-60 pieces or 5-30 pieces. The user is typically instructed to repeat the contacting and incubation steps a number of times, depending, for instance, on the user's degree of tooth staining or desired degree of tooth whitening.

In a further optional step, the whitening composition is exposed to light in order to activate the whitening composition and accelerate tooth whitening. For example, light is directed at a gum or candy delivery device for a period of time sufficient to activate the whitening agent. Exposure of the whitening composition may be prior to the user's chewing or dissolving the gum or candy in the mouth. In an alternative option, the whitening composition is exposed to light in place on a user's tooth following release from the gum or candy in the user's mouth, preferably in place on the user's teeth.

Commercial Package

A commercial package provided by the present invention includes a mechanical dispensing device having a whitening composition disposed therein and instructions for use thereof. Optionally included is a separator for separation of lips, tongue and cheeks from teeth to be whitened. Another option is to include a dental apparatus as described herein including a support structure and a light source for use in activating a whitening composition in the mouth.

In one embodiment of an inventive commercial package, an apparatus having a support structure a first light source for use in activating a whitening composition in the mouth is provided, along with a second light source for activating the first light source. For example, as shown in FIG. 15, a container A contains an apparatus 8000 provided as a moldable sheet material having a shape which generally conforms to the shape of a human dental arch, the moldable support is transformed to a custom fit dental tray by direct application to the user's dentition and molding in place. The moldable apparatus includes a first light source, preferably a particulate phosphorescent light source, disposed on a surface of the moldable sheet material as shown. Further preferred is a moldable apparatus having a hexagonal textured surface as described herein and including a particulate phosphorescent light source, disposed on the textured surface. A second light source, shown at 8004 is provided in the commercial package. The second light source emits light which excites the phosphorescent light source disposed on the support structure, such that the excited phosphorescent light source emits light. In a preferred embodiment, the second light source is a diode light source, especially an LED, emitting light at a wavelength ranging between 300-900 nanometers, depending on the type of phosphorescent source used. Particularly preferred is a second light source emitting light having a wavelength ranging between 390-430, preferably 400-410 nanometers, where the phosphorescent material is excited by this wavelength. It will be evident to one of skill in the art that a second light source emitting light with a wavelength between 300-900 nanometers is included to excite a first light source excited in this range. The exemplary second light source 8004 is a portable hand operated diode source including a battery.

Any patents or publications mentioned in this specification are herein incorporated by reference to the same extent as if each individual publication was specifically and individually indicated to be incorporated by reference. Further, U.S. patent application Ser. No. 10/872,256; U.S. Provisional Patent Application Ser. No. 60/479,801; and U.S. Pat. No. 7,645,137 are hereby incorporated by reference in their entirety.

One skilled in the art will readily appreciate that the present invention is well adapted to carry out the disclosed objects and obtain the ends and advantages set forth herein. The present methods, apparatus, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A process of whitening a tooth, comprising the steps of:
providing a delivery device having a push-button, twist-turn or lever, and wherein a single incremental movement of the push-button, twist-turn or lever mechanically dispenses a predetermined amount of a whitening composition to an applicator tip;
dispensing the predetermined amount of the whitening composition to the applicator tip by moving an expelling platform incrementally in association with a ratcheting mechanism;
applying the predetermined amount of the whitening composition disposed on the applicator tip to a tooth to be whitened;
exposing the whitening composition to light emitted from a phosphorescent light source; and
allowing the whitening composition to remain in contact with the tooth for a period of time sufficient to whiten the tooth.

2. The process of claim 1, wherein the predetermined amount ranges between 1-500 microliters.

3. The process of claim 1, wherein the predetermined amount ranges between 10-100 microliters.

4. The process of claim 1, wherein the whitening composition is exposed to the light prior to applying the amount of whitening composition disposed on the applicator tip to the tooth to be whitened.

5. The process of claim 1, wherein the whitening composition is exposed to the light after applying the amount of whitening composition disposed on the applicator tip to the tooth to be whitened.

6. The process of claim 1, wherein the whitening composition is exposed to the light during application the amount of whitening composition disposed on the applicator tip to the tooth to be whitened.

7. The process of claim 1, wherein the phosphorescent light source is disposed on the mechanical dispensing device.

8. The process of claim 1, wherein the phosphorescent light source is disposed in the whitening composition.

9. The process of claim 1, wherein the whitening composition comprises an oxidizing agent and/or a peroxide.

10. The process of claim 1, wherein the predetermined amount is dependent on a viscosity or concentration of the whitening composition.

11. The process of claim 1, wherein the whitening composition comprises a therapeutic agent selected from the group consisting of: a toothpaste, a mouthwash, an anti-plaque agent, an anesthetic, a desensitizing agent, an analgesic, an antibiotic, an antifungal, an antimicrobial, an antiviral, an anti-inflammatory agent, a steroid, a remineralizing agent an anticariogenic agent and a combination thereof.

12. The process of claim 1, further comprising the step of providing a dental apparatus, the dental apparatus comprising:
a support structure adapted to be placed entirely within a user's mouth; and
wherein the phosphorescent light source is disposed on or in the support structure such that the light emitted from the phosphorescent light source impinges on the dental whitening composition on the tooth to be whitened.

13. The process of claim 12, wherein the support structure is moldable to conform to the user's dentition and adapted to fit entirely within the user's mouth during use, the support structure is moldable at room temperature, without the addition of heat or is moldable using finger pressure.

14. The process of claim 13, further including the step of molding the support structure into a dental tray conforming to the user's dentition.

15. The process of claim 13, wherein the support structure includes a textured surface defining a plurality of individual cells having a configuration capable of contacting at least the tooth when the support structure is placed in the mouth, the cells each defining a depression having a configuration capable of receiving the whitening composition and/or disposition of light.

16. The process of claim 13, wherein the dental whitening composition is in contact with the support structure.

17. The process of claim 1, wherein the ratcheting mechanism includes a ratchet piece having a portion engageable with a complementary ratchet piece, and a spring biasing at least a portion of the ratcheting mechanism.

* * * * *